US011592504B2

(12) United States Patent
Yang et al.

(10) Patent No.: US 11,592,504 B2
(45) Date of Patent: Feb. 28, 2023

(54) MRI COIL WITH A RF SHIELD FOR RADIATION OR X-RAY APPLICATIONS

(71) Applicant: Quality Electrodynamics, LLC, Mayfield Village, OH (US)

(72) Inventors: Xiaoyu Yang, Indiana, PA (US); Samuel Musilli, Cleveland Heights, OH (US); Christopher J. Allen, Euclid, OH (US); Labros Petropoulos, Chardon, OH (US)

(73) Assignee: Quality Electrodynamics, LLC, Mayfield Village, OH (US)

( * ) Notice: Subject to any disclaimer, the term of this patent is extended or adjusted under 35 U.S.C. 154(b) by 24 days.

(21) Appl. No.: 17/202,793

(22) Filed: Mar. 16, 2021

(65) Prior Publication Data

US 2021/0302514 A1    Sep. 30, 2021

Related U.S. Application Data

(60) Provisional application No. 63/008,136, filed on Apr. 10, 2020, provisional application No. 63/000,090, filed on Mar. 26, 2020.

(51) Int. Cl.
*G01R 33/34* (2006.01)
*G01R 33/483* (2006.01)
*G01R 33/422* (2006.01)

(52) U.S. Cl.
CPC . *G01R 33/34076* (2013.01); *G01R 33/34092* (2013.01); *G01R 33/422* (2013.01); *G01R 33/4831* (2013.01)

(58) Field of Classification Search
CPC ........ G01R 33/34076; G01R 33/34092; G01R 33/422; G01R 33/4831
See application file for complete search history.

(56) References Cited

U.S. PATENT DOCUMENTS

| | | | |
|---|---|---|---|
| 4,694,255 A | 9/1987 | Hayes | |
| 6,029,082 A * | 2/2000 | Srinivasan | ....... G01R 33/34046 324/318 |
| 6,169,401 B1 * | 1/2001 | Fujita | ................. G01R 33/3678 324/318 |
| 6,316,941 B1 * | 11/2001 | Fujita | ............... G01R 33/34046 324/318 |

(Continued)

*Primary Examiner* — Dixomara Vargas
(74) *Attorney, Agent, or Firm* — Eschweiler & Potashnik, LLC

(57) ABSTRACT

Various embodiments of the present disclosure are directed towards a magnetic resonance imaging (MRI) radio frequency (RF) coil. The MRI RF coil comprises a first conductive ring and a second conductive ring. A plurality of rung groups extend between the first and second conductive rings. The plurality of rung groups are spaced uniformly about the first conductive ring. Each of the plurality of rung groups comprises a plurality of conductive rungs extending between and connected to the first and second conductive rings. The plurality of conductive rungs of each of the plurality of rung groups are azimuthally separated from one another by a first azimuth angle. Each of the plurality of rung groups is separated from a neighboring rung group by a spacing that forms a window. Each of the windows have a second azimuth angle that is greater than the first azimuth angle.

20 Claims, 17 Drawing Sheets

(56) References Cited

U.S. PATENT DOCUMENTS

| | | | |
|---|---|---|---|
| 6,404,201 B1* | 6/2002 | Boskamp | G01R 33/34076 324/318 |
| 2004/0015074 A1* | 1/2004 | Srinivasan | G01R 33/34046 324/318 |
| 2004/0075437 A1* | 4/2004 | Srinivasan | G01R 33/34046 324/318 |
| 2009/0021255 A1* | 1/2009 | DeVries | G01R 33/3415 324/318 |
| 2010/0117642 A1* | 5/2010 | Zhai | G01R 33/422 324/318 |
| 2012/0086452 A1* | 4/2012 | Dohata | G01R 33/3456 324/318 |
| 2012/0262173 A1* | 10/2012 | Soutome | G01R 33/34076 324/309 |
| 2012/0268132 A1* | 10/2012 | Zhu | G01R 33/3692 324/322 |
| 2013/0119991 A1* | 5/2013 | Soutome | G01R 33/34 324/322 |
| 2014/0055136 A1* | 2/2014 | Leussler | G01R 33/3664 324/309 |
| 2014/0194727 A1* | 7/2014 | Boskamp | G01R 33/0052 324/322 |
| 2014/0253126 A1* | 9/2014 | Habara | G01R 33/34092 324/322 |
| 2018/0246179 A1* | 8/2018 | Zhai | G01R 33/3875 |
| 2019/0049535 A1* | 2/2019 | Saha | A61B 5/055 |
| 2019/0113586 A1* | 4/2019 | Lips | G01R 33/3453 |
| 2019/0137579 A1* | 5/2019 | Fukushima | G01R 33/34076 |
| 2019/0212401 A1* | 7/2019 | Makarov | A61N 1/40 |
| 2019/0317166 A1* | 10/2019 | Imai | G01R 33/3657 |
| 2019/0339345 A1* | 11/2019 | Leussler | G01R 33/3628 |

* cited by examiner

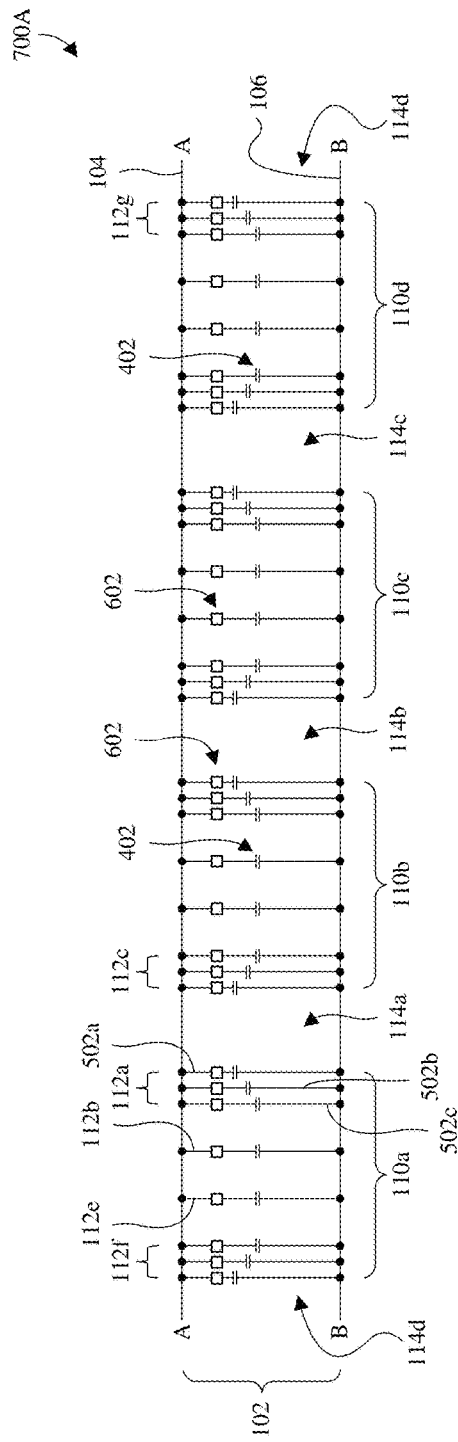
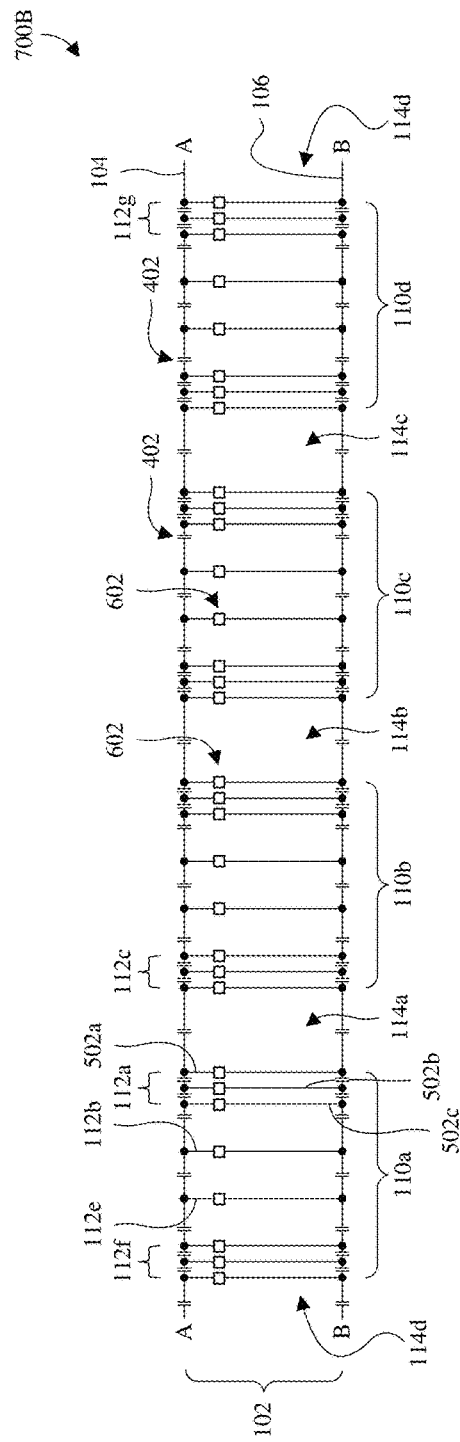
Fig. 7A
Fig. 7B

MRI COIL WITH A RF SHIELD FOR RADIATION OR X-RAY APPLICATIONS

REFERENCE TO RELATED APPLICATIONS

This application claims the benefit of U.S. Provisional Application No. 63/000,090, filed Mar. 26, 2020 (entitled "AN MRI WHOLE BODY COIL WITH A BUILT-IN RF SHIELD FOR RADIATION OR X-RAY APPLICATIONS"), and further claims the benefit of U.S. Provisional Application No. 63/008,136, filed on Apr. 10, 2020 (entitled "AN MRI WHOLE BODY COIL WITH A BUILT-IN RF SHIELD FOR RADIATION OR X-RAY APPLICATIONS"). The contents of the above-referenced Provisional Patent Applications are hereby incorporated by reference in their entirety.

BACKGROUND

A birdcage coil is a type of coil that is often utilized as a system built-in transmit/receive coil-whole body coil (WBC) for magnetic resonance imaging (MRI) systems from low field to high field, such as 0.7 tesla (T), 1.5 T, 3 T, etc. A birdcage coil comprises two conductive rings with a plurality of conductive rungs extending between the two conductive rings. Typically, the number of conductive rungs is a multiple of four, and the conductive rungs are positioned uniformly along the azimuthal direction (e.g., the azimuthal direction of the conductive rings). The $B_1$ field uniformity from a birdcage coil in the Field-of-View (FOV) is important (e.g., to generate high quality images). Typically, a four-rung birdcage coil exhibits a worse $B_1$ field uniformity in the FOV than an equally spaced 16-rung birdcage coil. As such, most WBCs have at least 16 conductive rings that are distributed uniformly along the azimuthal direction.

An MRI scanner has a set of gradient coils (e.g., x, y, and z gradient coils). These gradient coils are typically located outside of the WBC. Gradient coils are typically made of copper wires and couple to the WBC. The gradient coils often negatively affect the WBC performance unless a mitigation technique is implemented.

A commonly used mitigation technique is for the MRI scanner to have a cylindrical RF shield between the gradient coils and the WBC. The RF shield is configured to provide two functions. The first function is to provide decoupling between the WBC and the gradient coils. The second function is for the RF shield to have a minimized eddy current from a strong gradient pulse. Typically, these two functions conflict with one another. One possible technique to mitigate the conflict between these two functions is to use a thin copper sheet as an RF shield, form many slots in the copper sheet, and strategically place capacitors at specific locations, such that the copper sheet operates like a whole copper sheet (e.g., as if the copper sheet was slot-free). The slots in the copper sheet help reduce the eddy currents. As such, the copper sheet operates as a good RF shield while reducing eddy currents.

BRIEF DESCRIPTION OF THE DRAWINGS

FIGS. 7A-7C illustrate various circuit schematics of some other embodiments of the birdcage coil of FIGS. 2A-2B.

DETAILED DESCRIPTION

Figure 1:
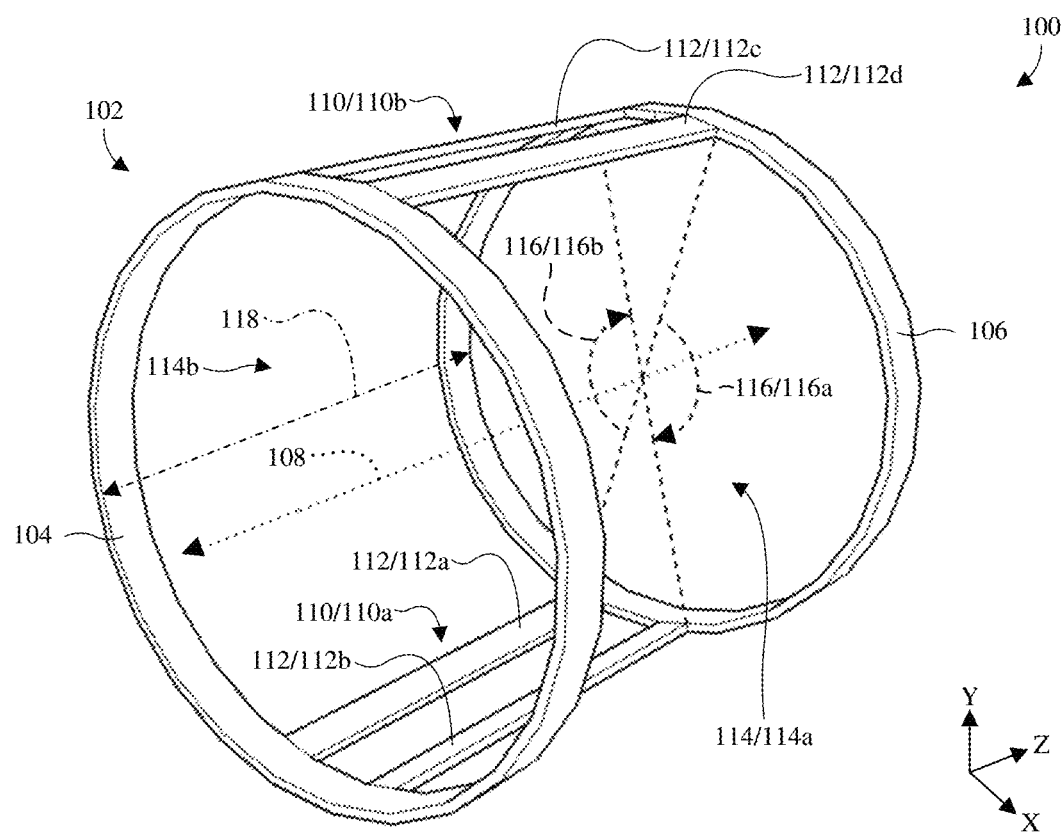
FIG. 1 illustrates a perspective view of some embodiments of a magnetic resonance imaging (MRI) radio frequency (RF) coil comprising a birdcage coil that has a plurality of windows and a plurality of rung groups.

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

As the medical field advances, new medical applications are continually being developed. Some of these new medical applications utilize magnetic resonance imaging (MRI) with other medical modalities, such as radiation therapy, computed tomography (CT), tomosynthesis, X-ray, or the like. In some of these new applications, radiation and/or X-ray beams pass through the system built-in transmit/receive coil-whole body coil (WBC) to reach a patient. Further, when a radiation and/or X-ray beam passes through the WBC, these applications may also depend on the beam attenuation being small and uniform in the beam-through area (e.g., the area in which the beam passes through the WBC). As such, these new modalities present new challenges in WBC design that current WBCs may not meet.

For example, some new medical modalities may depend on good $B_1$ field uniformity in the Field-of-View (FOV) while also having relatively large openings in the WBC (e.g., openings having an azimuth of at least 22.5 degrees and a length that is at least 25 percent of the length of the WBC) so that a beam may pass through WBC with small and uniform beam attenuation. To achieve good $B_1$ field uniformity in the FOV, typical WBCs comprise greater than or equal to sixteen (16) conductive rungs that are distributed uniformly along the azimuthal direction of the WBC. However, such a WBC configuration does not provide large enough openings between the conductive rungs so that the beam may pass through the WBC with small and uniform beam attenuation. One partial solution may be to reduce the number of conductive rungs, however, such a partial solution negatively affects $B_1$ field uniformity in the FOV (e.g., $B_1$ field uniformity worsens as the number of conductive rungs decreases).

Various embodiments of the present disclosure are directed toward a magnetic resonance imaging (MRI) radio frequency (RF) coil (e.g., a system built-in transmit/receive coil-whole body coil (WBC)) having a plurality of windows and a plurality of rung groups. The MRI RF coil comprises a first conductive ring and a second conductive ring. The second conductive ring is spaced from the first conductive ring. A plurality of rungs groups extend between the first and second conductive rings. Each of the rung groups comprise a plurality of conductive rungs that extend between and are connected to the first and second conductive rings. Further, each of the rung groups are azimuthally separated from a neighboring rung group by a spacing that forms a window.

Because the plurality of conductive rungs are grouped into rung groups that are azimuthally separated by windows, the $B_1$ field uniformity in the FOV is good (e.g., greater than or equal to about 0.655) and a beam may pass through the MRI coil with small and uniform beam attenuation (e.g., due the windows having an azimuth of at least 22.5 degrees). More specifically, by grouping the conductive rungs into the rung groups, the MRI coil may comprise a same number of conductive rungs as a typical WBC, while having larger beam-through areas than the typical WBC. Surprisingly, although the conductive rungs of the MRI coil are spaced nearer together than a typical WBC coil (e.g., spaced together in the rung groups rather than being uniformly spaced about the WBC), the $B_1$ field generated by the MRI coil has a field uniformity that is almost as good as the typical WBC. For example, a typical 16-rung WBC coil may generate a $B_1$ field with a field uniformity of about 0.656, whereas a 16-rung MRI coil of the present disclosure may generate a $B_1$ field with a field uniformity of about 0.655. Accordingly, the MRI coil of the present disclosure may increase the number of new medical modalities that utilize MRI.

FIG. 1 illustrates a perspective view 100 of some embodiments of a magnetic resonance imaging (MRI) RF coil comprising a birdcage coil 102 that has a plurality of windows 114 and a plurality of rung groups 110.

As shown in the perspective view 100 of FIG. 1, the MRI RF coil comprises a birdcage coil 102. The birdcage coil 102 comprises a first conductive ring 104 and a second conductive ring 106. The first conductive ring 104 and the second conductive ring 106 are spaced apart (along the z-axis). In some embodiments, the first conductive ring 104 and the second conductive ring 106 are concentric about an axis 108.

A plurality of rung groups 110 extend (along the z-axis) between the first conductive ring 104 and the second conductive ring 106. The plurality of rung groups 110 comprise at least two (2) individual rung groups. For example, as shown in the perspective view 100 of FIG. 1, the birdcage coil 102 comprise a first rung group 110a and a second rung group 110b. The plurality of rung groups 110 are spaced uniformly about the first conductive ring 104 and the second conductive ring 106.

Each of the plurality of rung groups 110 comprise a plurality of conductive rungs 112. The plurality of conductive rungs 112 extend between (along the z-axis) and are connected to the first conductive ring 104 and the second conductive ring 106. Each of the plurality of rung groups 110 comprise at least two individual conductive rungs that extend in parallel (along the z-axis) between the first conductive ring 104 and the second conductive ring 106. For example, the first rung group 110a comprises a first conductive rung 112a and a second conductive rung 112b, and the second rung group 110b also comprises a first conductive rung 112c and a second conductive rung 112d. Because the birdcage coil 102 of FIG. 1 has four (4) conductive rungs, the birdcage coil 102 may be referred to as a 4-rung birdcage coil 102 (and/or a 4-rung MRI birdcage coil). The first conductive ring 104, the second conductive ring 106, and the plurality of conductive rungs 112 are defined by one or more conductors (e.g., copper wire, coaxial cable, copper sheets, silver wire, conductive traces on a flexible printed circuit board (PCB), printed conductors (e.g., screen-printed coils), etc.).

Each of the plurality of rung groups 110 are separated azimuthally from a neighboring rung group by an opening that forms a window 114. The windows are areas of free space (e.g., air) that do not comprise any portions of the first conductive ring 104, any portions of the second conductive ring 106, or any portions of the plurality of conductive rungs 112. The windows 114 are configured so that a radiation and/or X-ray beam (or some other electromagnetic radiation beam) may be passed through the birdcage coil 102. Each of the windows 114 are defined by an edge of two neighboring rung groups.

For example, as shown in the perspective view 100 of FIG. 1, the first rung group 110a neighbors the second rung group 110b, and vice versa. The first rung group 110a is azimuthally separated from the second rung group 110b by a first window 114a, and the second rung group 110b is azimuthally separated from the first rung group 110a by a second window 114b. In other words, the first rung group 110a is separated azimuthally from the second rung group 110b by both the first window 114a and the second window 114b, and the second rung group 110b is also separated azimuthally from the first rung group 110a by both the first window 114a and the second window 114b. The first window 114a is defined by a first edge of the first rung group 110a and a first edge of the second rung group 110b. The second window 114b is defined by a second edge of the first rung group 110a opposite the first edge of the first rung group 110a and a second edge of the second rung group 110b opposite the first edge of the second rung group 110b.

Each of the windows 114 wrap around the axis 108 by an azimuth angle 116. For example, the first window 114a wraps around the axis 108 by a first azimuth angle 116a (e.g., the first window 114a has a first azimuth that corresponds to the first azimuth angle 116a) and the second window 114b wraps around the axis 108 by a second azimuth angle 116b (e.g., the second window 114b has a second azimuth that corresponds to the second azimuth angle 116b). The azimuth angle 116 for each of the windows 114 is at least 22.5 degrees. In some embodiments, the azimuth angle 116 for each of the windows 114 is less than 180 degrees. In some embodiments, an electromagnetic beam (e.g., a radiation and/or X-ray beam) may pass through one or more of the windows 114 due to the windows 114 having an azimuth angle that is at least 22.5 degrees.

The first conductive ring 104 has an outer edge. The second conductive ring 106 has an outer edge. The outer edge of the first conductive ring 104 and the outer edge of the second conductive ring 106 face away from one another. The outer edge of the first conductive ring 104 and the outer edge of the second conductive ring 106 are laterally spaced (along the z-axis) by a distance 118. Each of the windows 114 extends laterally (along the z-axis) by at least about 25 percent of the distance 118. In some embodiments, each of the windows 114 extends laterally (along the z-axis) about 50 percent of the distance 118.

The birdcage coil 102 is configured to generate a $B_1$ magnetic field in a Field-of-View (FOV). Because the plurality of rung groups 110 comprise the plurality of conductive rungs 112 and are azimuthally separated by the windows 114, the $B_1$ field uniformity in the FOV is good (e.g., about as good as a typical WBC having a same number of conductive rungs) and an electromagnetic beam (e.g., radiation and/or X-ray beam) may pass through the birdcage coil 102 with minimum (or no) beam attenuation (e.g., a small and uniform beam attenuation). More specifically, because the plurality of conductive rungs 112 are grouped together in the plurality of rung groups 110, the birdcage coil 102 may comprise a same number of conductive rungs as a typical MRI coil (e.g., a birdcage WBC having conductive rungs that are azimuthally spaced a same distance apart), while having larger beam-through areas than the typical MRI coil. Surprisingly, although the plurality of conductive rungs 112 of the birdcage coil 102 may be spaced nearer together than a typical MRI coil (e.g., spaced together in the rung groups 110 rather than being uniformly spaced about the WBC), the $B_1$ field generated by the birdcage coil 102 has a field uniformity that is as good (or about as good) as the typical MRI coil. Accordingly, the birdcage coil 102 may increase the number of new medical modalities that utilize MRI.

In some embodiments, to compare whether the birdcage coil 102 generates a $B_1$ field having a field uniformity that is as good (or about as good) as the $B_1$ field generated by a typical MRI coil, parameters for the birdcage coil 102 and the typical MRI coil are defined, and the $B_1$ uniformities of the birdcage coil 102 and the typical MRI coil are compared for a given number of total conductive rungs. For example, the parameters may be defined as: (1) MRI coil radius (e.g., radius of birdcage coil 102 and the radius of typical MRI coil) of 1 arbitrary unit (arb. unit); (2) MRI coil length of 0.8 arb. unit; (3) FOV of 0.45 in the x-direction; (4) FOV of 0.45 in the y-direction; and (5) FOV of 0.4 in the z-direction. The uniformity may then be calculated by following the National Electrical Manufacturers Association (NEMA) definition of:

$$1 - \frac{(\text{max.value in } FOV - \text{min.value in } FOV)}{(\text{max.value in } FOV + \text{min.value in } FOV)}$$

Based on the above parameters, a typical 16-rung WBC coil may have a uniformity of about 0.656 in a 40 centimeter (cm) by 40 cm by 45 cm phantom, whereas the birdcage coil 102 having 16 individual conductive rungs (e.g., the plurality of conductive rungs 112 comprises 16 individual conductive rungs) may have a uniformity of about 0.655 in the 40 cm by 40 cm by 45 cm phantom, which is about as good as the typical 16-rung WBC. As such, the birdcage coil 102 generates a $B_1$ field that has a $B_1$ field uniformity that is as good (or about as good) as the $B_1$ field generated by the typical MRI coil.

In some embodiments, the MRI RF coil is a system built-in transmit/receive coil-whole body coil (WBC) for MRI systems from low field to high field, such as 0.7 tesla (T), 1.5 T, 3 T, etc. It will be appreciated that, in other embodiment, the MRI RF coil may be other types of MRI coils (e.g., a knee coil, a head coil, etc.). It will also be appreciated that not only may the MRI RF coil be a transmit (Tx)/receive (Rx) coil (e.g., configured to operate in both a transmit and a receive mode), but the MRI RF coil may be a Tx-only coil (e.g., configured to operate only in a transmit mode) or a Rx-only coil (e.g., configured to operate only in a receive mode).

Figure 2B:
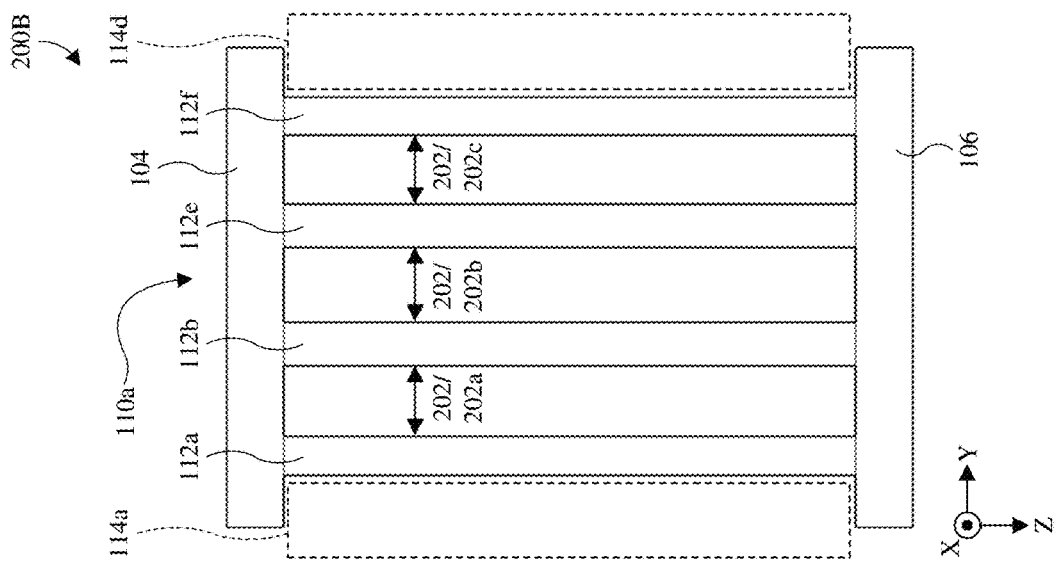
FIGS. 2A-2B illustrate various views of some other embodiments of the MRI RF coil of FIG. 1.
Figure 2A:
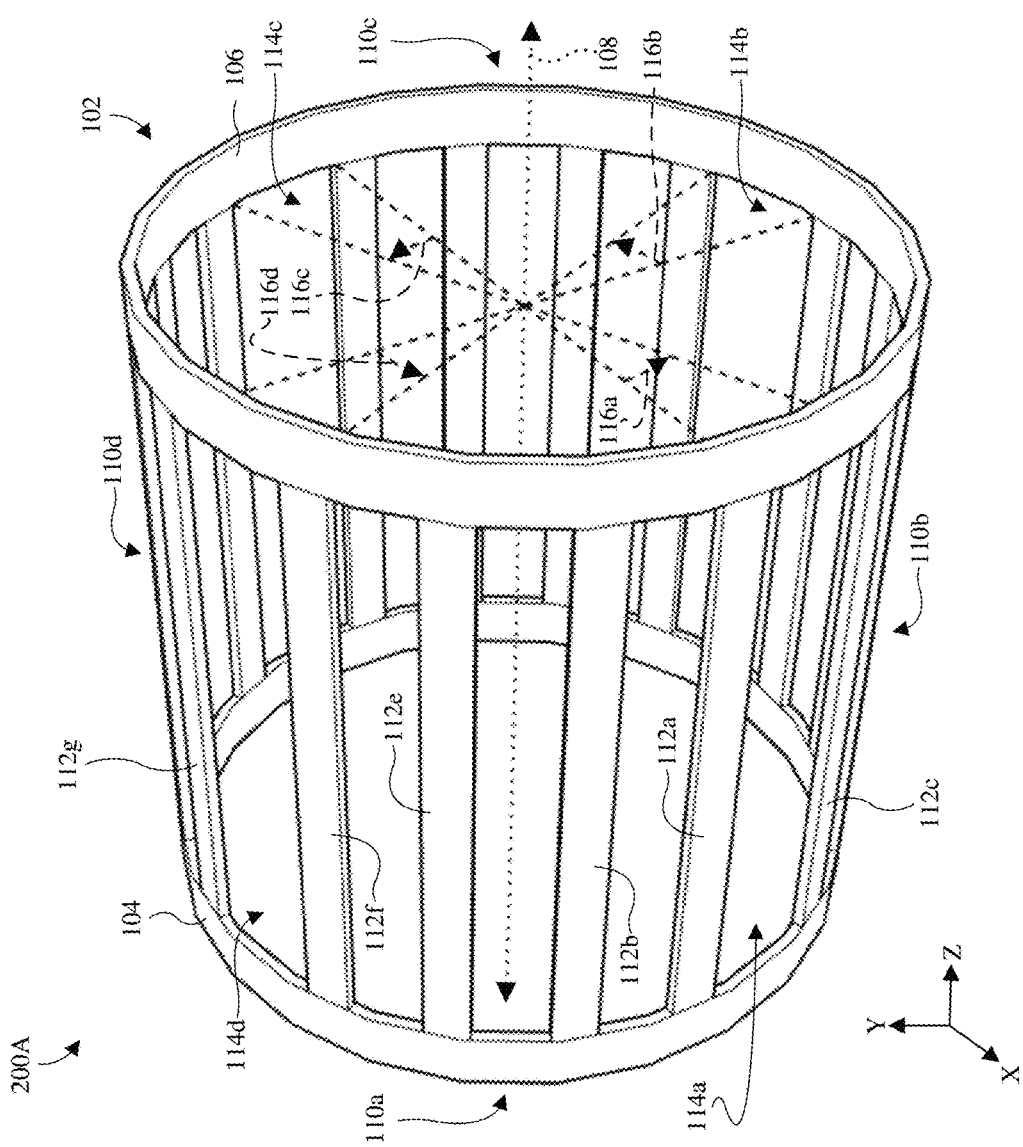

FIGS. 2A-2B illustrate various views 200A-200B of some other embodiments of the MRI RF coil of FIG. 1. FIG. 2A illustrates a perspective view 200A of some other embodiments of the MRI RF coil of FIG. 1. FIG. 2B illustrates a magnified two-dimensional (2D) side view 200B of the first rung group 110a of the MRI RF coil of FIG. 2A.

As shown in the various views 200A-200B of FIGS. 2A-2B, the birdcage coil 102 comprises a plurality of rung groups 110. For example, the birdcage coil comprises a first rung group 110a, a second rung group 110b, a third rung group 110c, and a fourth rung group 110d. The first rung group 110a is azimuthally separated from the second rung group 110b by a first window 114a. The second rung group 110b is azimuthally separated from the third rung group 110c by a second window 114b. The third rung group 110c is azimuthally separated from the fourth rung group 110d by a third window 114c. The fourth rung group 110d is azimuthally separated from the first rung group 110a by a fourth window 114d.

In some embodiments, the birdcage coil 102 comprises N rung groups and M windows, where N equals M. For example, as shown in the various views 200A-200B of FIGS. 2A-2B, the birdcage coil 102 comprises four rung groups (N=4) and four windows (M=4). While the birdcage coil 102 of FIGS. 2A-2B comprises four rung groups and four windows, it will appreciated that the birdcage coil 102 may comprise any number of rung groups and windows that is greater than or equal to two (e.g., the birdcage coil 102 may comprise 2 windows and 2 rung groups, 3 windows and 3 rung groups, 5 windows and 5 rung groups, etc.). It will also be appreciated that the rung groups 110 may comprise any number of individual rungs that is greater than or equal to two conductive rungs (e.g., each of the rungs groups 110 may comprise 2 conductive rungs, 3 conductive rungs, 4 conductive rungs, 5 conductive rungs, etc.).

Each of the plurality of rung groups 110 comprise a plurality of conductive rungs 112. For example, the first rung group 110a comprises a first conductive rung 112a, a second conductive rung 112b, a third conductive rung 112e, and a fourth conductive rung 112f. The second conductive rung 112b and the third conductive rung 112e of the first rung group 110a are disposed between (azimuthally between) the first conductive rung 112a and the fourth conductive rung 112f of the first rung group 110a.

Conductive edge rungs of each of the rung groups 110 define edges of the windows 114. For example, the first conductive rung 112a of the first rung group 110a is a first conductive edge rung of the first rung group 110a and the fourth conductive rung 112f of the first rung group 110a is a second conductive edge rung of the first rung group 110a. The second rung group 110b comprises a first conductive rung 112c that is a first conductive edge rung of the second rung group 110b. The fourth rung group 110d comprises a first conductive rung 112g that is a first conductive edge rung of the fourth rung group 110d. A sidewall of the first conductive rung 112a of the first rung group 110a and a sidewall of the first conductive rung 112c of the second rung group 110b define opposite edges of the first window 114a. A sidewall of the fourth conductive rung 112f of the first rung group 110a and a sidewall of the first conductive rung 112g of the fourth rung group 110d define opposite edges of the fourth window 114d.

Each of the windows 114 wrap around an axis 108 by an azimuth angle 116. For example, the first window 114a wraps around the axis by a first azimuth angle 116a (e.g., the first window 114a has a first azimuth that corresponds to the first azimuth angle 116a), the second window 114b wraps around the axis 108 by a second azimuth angle 116b, the third window 114c wraps around the axis 108 by a third azimuth angle 116c, and the fourth window 114d wraps around the axis 108 by a fourth azimuth angle 116d. The azimuth angle 116 for each of the windows 114 is at least 22.5 degrees. In some embodiments, the azimuth angle 116 for each of the windows 114 is between about 180 degrees and about 22.5 degrees. In further embodiments, each of the windows 114 have a same azimuth angle. For example, the first azimuth angle 116a, the second azimuth angle 116b, the third azimuth angle 116c, and the fourth azimuth angle 116d are each 60 degrees.

Each of the plurality of conductive rungs 112 of each rung group 110 are azimuthally separated from one another. For example, the first conductive rung 112a, the second conductive rung 112b, the third conductive rung 112e, and the fourth conductive rung 112f of the first rung group 110a are azimuthally separated from one another. Each of the plurality of conductive rungs 112 of a given rung group 110 are separated azimuthally from a neighboring conductive rung of the given rung group 110 by an azimuth angle 202. For example, the first conductive rung 112a is azimuthally spaced from the second conductive rung 112b by a first azimuth angle 202a, the second conductive rung 112b is azimuthally spaced from the third conductive rung 112e by a second azimuth angle 202b, and the third conductive rung 112e is azimuthally spaced from the fourth conductive rung 112f by a third azimuth angle 202c. The azimuth angle 202 (or each of the azimuth angles 202) is less than the azimuth angle 116 (or each of the azimuth angles 116).

In some embodiments, the azimuth angle 202 is the same for each of the plurality of conductive rungs 112 of a given rung group. For example, the first azimuth angle 202a, the second azimuth angle 202b, and the third azimuth angle 202c are the same. In further embodiments, the azimuth angle 202 is the same for each of the plurality of conductive rungs 112 of each of the rung groups 110. In other words, the conductive rungs of the birdcage coil 102 are distributed equally in non-windowed areas from the edge of one window to the edge of a neighboring window.

In some embodiments, the birdcage coil 102 of FIGS. 2A-2B may be referred to as a 16-rung birdcage coil (e.g., because the birdcage coil 102 comprises 16 individual conductive rungs). While the birdcage coil 102 is illustrated in FIGS. 2A-2B having a total of 16 conductive rungs, it will be appreciated the birdcage coil 102 may comprise any other number of total conductive rungs. In some embodiments, the birdcage coil 102 comprises a total number of conductive rungs that is a multiple of four (e.g., 4 conductive rungs, 8 conductive rungs, 12 conductive rungs, 16 conductive rungs, etc.).

Figure 3A:
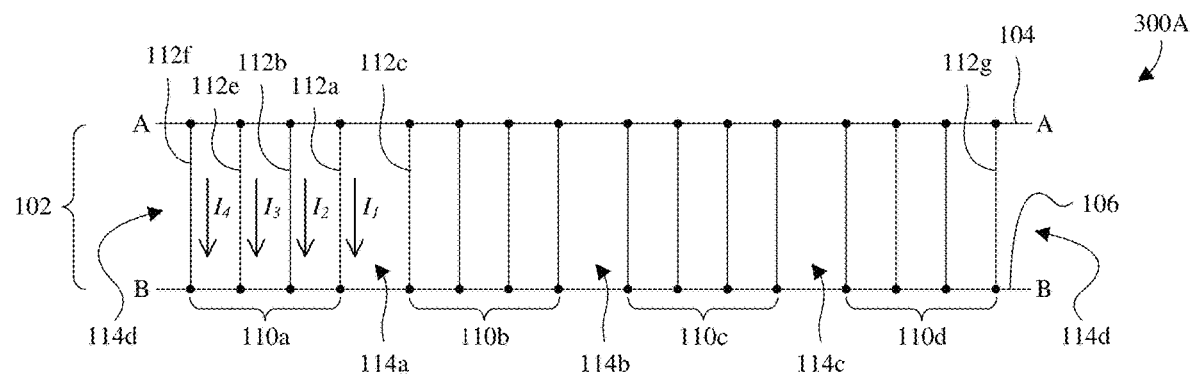
FIGS. 3A-3B illustrate various circuit schematics of some embodiments of the birdcage coil of FIGS. 2A-2B.
Figure 3B:
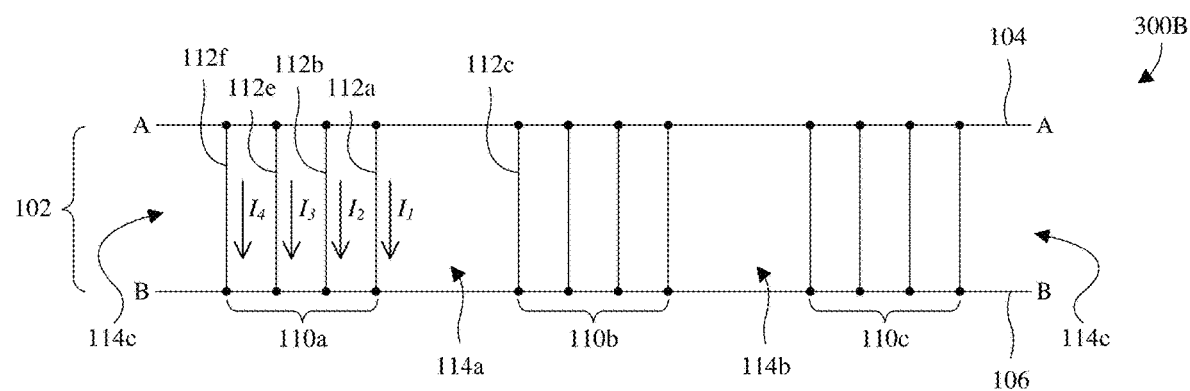

FIGS. 3A-3B illustrate various circuit schematics 300A-300B of some embodiments of the birdcage coil 102 of FIGS. 2A-2B. FIG. 3A illustrates a circuit schematic 300A of a first embodiment of the birdcage coil 102 of FIGS. 2A-2B. FIG. 3B illustrates a circuit schematic 300B of a second embodiment of the birdcage coil 102 of FIGS. 2A-2B in which the windows 114 of the second embodiment of the birdcage coil 102 have a larger azimuth angle 116 (see, e.g., FIGS. 2A-2B) than the windows 114 of the first embodiment of the birdcage coil 102.

As shown in the circuit schematic 300A of FIG. 3A, a first rung group 110a comprises a first conductive rung 112a, a second conductive rung 112b, a third conductive rung 112e, and a fourth conductive rung 112f. The first conductive rung 112a is configured to carry a first current $I_1$ from the first conductive ring 104 to the second conductive ring 106, or vice versa. The second conductive rung 112b is configured to carry a second current $I_2$ from the first conductive ring 104 to the second conductive ring 106, or vice versa. The third conductive rung 112e is configured to carry a third current $I_3$ from the first conductive ring 104 to the second conductive ring 106, or vice versa. The fourth conductive rung 112f is configured to carry a fourth current $I_4$ from the first conductive ring 104 to the second conductive ring 106, or vice versa. In some embodiments, the first current $I_1$, the second current $I_2$, the third current $I_3$, and the fourth current $I_4$ are the same. In other embodiments, one or more of the first current $I_1$, the second current $I_2$, the third current $I_3$, and the fourth current $I_4$ are different from one another.

The first current $I_1$ has a first electrical phase, the second current $I_2$ has a second electrical phase, the third current $I_3$ has a third electrical phase, and the fourth current $I_4$ has a fourth electrical phase. In some embodiments, the first electrical phase, the second electrical phase, the third electrical phase, and the fourth electrical phase match the azimuth angle (from a single reference point) of the first conductive rung 112a, the second conductive rung 112b, the third conductive rung 112e, and the fourth conductive rung 112f, respectively. For example, if the first conductive rung 112a has an azimuth angle of 90 degrees from a reference point, the second conductive rung 112b has an azimuth angle of 95 degrees from the reference point, the third conductive rung 112e has an azimuth angle of 100 degrees from the reference point, and the fourth conductive rung 112f has an azimuth angle of 105 degrees from the reference point, then the first electrical phase is 90 degrees out of phase from a reference electrical phase, the second electrical phase is 95 degrees out of phase from the reference electrical phase, the third electrical phase is 100 degrees out of phase from the reference electrical phase, and the fourth electrical phase is 105 degrees out of phase from the reference electrical phase. In such embodiments, the birdcage coil 102 can be quadrature driven. The first electrical phase, the second electrical phase, the third electrical phase, and the fourth electrical phase may be set to match the azimuth angle (from a single reference point) of the first conductive rung 112a, the second conductive rung 112b, the third conductive rung 112e, and the fourth conductive rung 112f, respectively, by strategically setting the values of capacitors disposed throughout the birdcage coil 102.

It will be appreciated that the above description of phases is merely an example, and the first phase, the second phase, the third phase, and the fourth phase may have different configurations to further optimize the birdcage coil 102. It will also be appreciated that, while the above currents and phases are described in relation to the conductive rungs of the first rung group 110a, each of the rung groups 110 of the birdcage coil 102 are configured to carry a current (with a phase) that is based on the above phase and current description. It will also be appreciated that the birdcage coil 102 may be driven in other ways (e.g., linearly).

In some embodiments, the conductive edge rungs of each of the rung groups 110 are configured to carry a larger current (e.g., a current with a larger magnitude) than non-edge conductive rungs of their respective rung group (see infra, e.g., capacitors 402). The conductive edge rungs are configured to carry larger currents than the non-edge conductive rungs of their respective rung group to compensate for any losses in the $B_1$ field caused by the windows 114. For example, the first current $I_1$ is greater than the second current $I_2$ and the third current $I_3$, and the fourth current $I_4$ is also greater than the second current $I_2$ and the third current $I_3$. In some such embodiments, the first current $I_1$ is the same as the fourth current $I_4$, and the second current $I_2$ is the same as the third current $I_3$. As such, any losses in the $B_1$ field which are caused by the first window 114a and the fourth window 114d may be minimized. It will be appreciated that any losses in the $B_1$ field may also be compensated due to a first conductive rung 112c of the second rung group 110b and a first conductive rung 112g of a fourth rung group 110d also being configured to carry a larger current than the non-edge conductive rungs of their respective rung groups.

As shown in the circuit schematic 300B of FIG. 3B, the birdcage coil 102 may be a 12-rung birdcage coil. In some embodiments, the 12-rung birdcage coil comprises three rung groups (e.g., the first rung group 110a, the second rung group 110b, and the third rung group 110c). In further embodiments, the 12-rung birdcage coil may also comprise three windows 114. It will be appreciated that the 12-rung birdcage coil may comprise a different number of rung groups (e.g., 2 rung groups, 4 rung groups, or the like) and/or different number of windows 114 (e.g., 2 windows, 4 windows, or the like).

In some embodiments, the azimuth angle 116 (see, e.g., FIGS. 2A-2B) of the windows 114 of the 12-rung birdcage coil may be greater than the azimuth angle 116 of a 16-rung birdcage coil. For example, as shown in the circuit schematic 300A of FIG. 3A, the birdcage coil 102 is a 16-rung birdcage coil. As shown in the various circuit schematics 300A-300B of FIG. 3A-3B, the windows 114 of the 16-rung birdcage coil have an azimuth angle 116 that is less than an azimuth angle 116 of the windows of the 12-rung birdcage coil. For example, the azimuth angle 116 of the windows 114 of the 16-rung birdcage coil may be about 22.5 degrees, whereas the azimuth angle 116 of the 12-run birdcage coil may be about 60 degrees. It will be appreciated that the above azimuth angles are merely examples, and the windows 114 of the 16-rung and the 12-rung birdcage coil (or some other numbered rung birdcage coil) may have a different azimuth angle that is between about 22.5 degrees and about 180 degrees. It will also be appreciated that the azimuth angle 202 between the individual conductive rungs 112 may affect the azimuth angle 116 of the windows 114, or vice versa (e.g., the larger that azimuth angle 116 the smaller the azimuth angle 202 (for a given birdcage coil having a predetermined number of rungs with predetermined widths)), or vice versa.

Figure 4A:
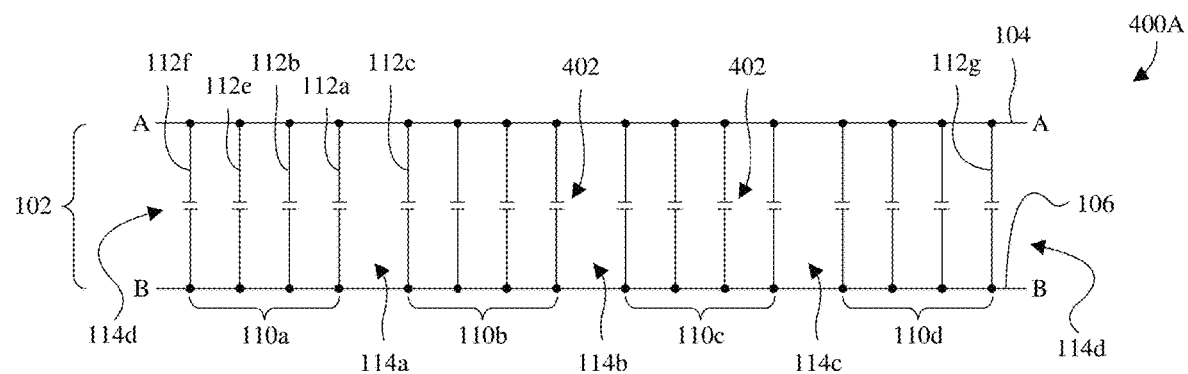
FIGS. 4A-4C illustrate various circuit schematics of some other embodiments of the birdcage coil of FIGS. 2A-2B.
Figure 4B:
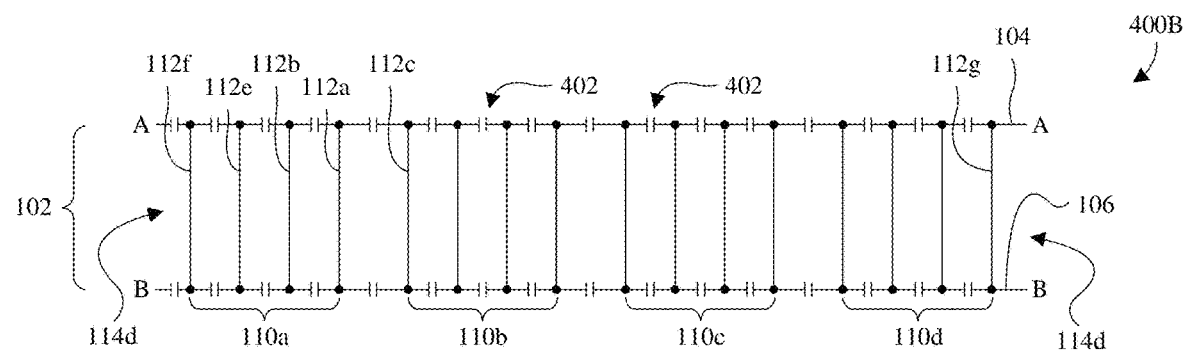
Figure 4C:
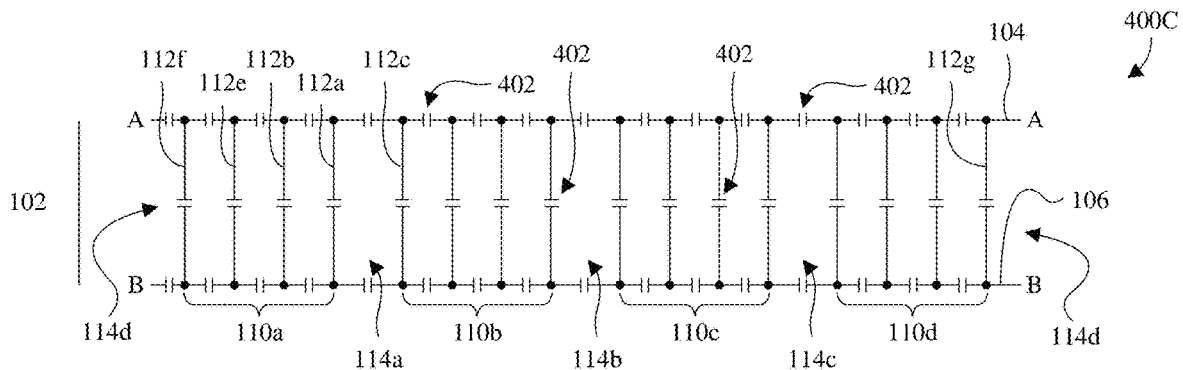

FIGS. 4A-4C illustrate various circuit schematics 400A-400C of some other embodiments of the birdcage coil 102 of FIGS. 2A-2B.

As shown in the various circuit schematics 400A-400C, the birdcage coil 102 may comprise a plurality of capacitors 402 disposed at specific locations on the birdcage coil 102. For example, as shown in the schematic view 400A, the capacitors 402 are disposed between a first conductive portion and a second conductive portion of the plurality of conductive rungs 112, respectively. For example, a first capacitor is disposed between a first conductive portion and a second conductive portion of the first conductive rung 112a of the first rung group 110a, and a second capacitor is disposed between a first conductive portion and a second conductive portion of the second conductive rung 112b of the first rung group 110a, and so forth. In such embodiments, the birdcage coil 102 is a low-pass MRI coil.

As shown in the schematic view 400B of FIG. 4B, in other embodiments, the capacitors 402 are disposed along the first conductive ring 104 and the second conductive ring 106 and between neighboring conductive rungs. For example, a first capacitor is disposed between a first conductive portion and a second conductive portion of the first conductive ring 104, where the first conductive portion and the second conductive portion of the first conductive ring 104 extend between the first conductive rung 112a and the second conductive rung 112b of the first rung group 110a, and a second capacitor is disposed between a first conductive portion and a second conductive portion of the second conductive ring 106, where the first conductive portion and the second conductive portion of the second conductive ring 106 extend between the first conductive rung 112a and the second conductive rung 112b of the first rung group 110a. In such embodiments, the birdcage coil 102 is a high-pass MRI coil.

As shown in the schematic view 400C of FIG. 4C, in other embodiments, some of the capacitors 402 are disposed along the first conductive ring 104 and the second conductive ring 106 and between neighboring conductive rungs, and some other of the capacitors 402 are disposed along the conductive rungs 112 and between the first conductive ring 104 and the second conductive ring 106. For example, a first capacitor is disposed between a first conductive portion and a second conductive portion of the first conductive rung 112a of the first rung group 110a; a second capacitor is disposed between a first conductive portion and a second conductive portion of the first conductive ring 104, where the first conductive portion and the second conductive portion of the first conductive ring 104 extend between the first conductive rung 112a and the second conductive rung 112b of the first rung group 110a; and a third capacitor is disposed between a first conductive portion and a second conductive portion of the second conductive ring 106, where the first conductive portion and the second conductive portion of the second conductive ring 106 extend between the first conductive rung 112a and the second conductive rung 112b of the first rung group 110a. In such embodiments, the birdcage coil 102 is a band-pass MRI coil.

Figure 5:
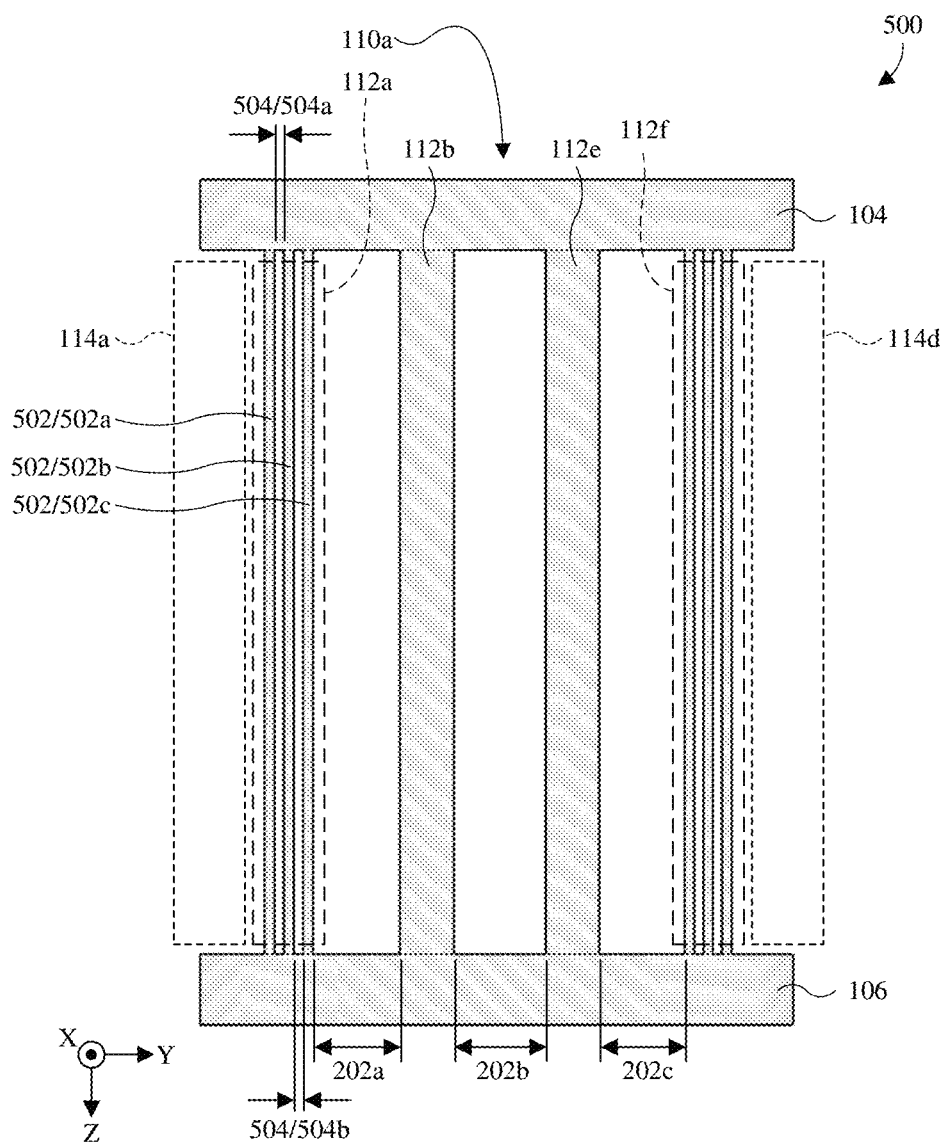
FIG. 5 illustrates a two-dimensional (2D) side view of some embodiments of a first rung group of the birdcage coil of FIGS. 2A-2B.

FIG. 5 illustrates a 2D side view 500 of some embodiments of a first rung group 110a of the birdcage coil 102 of FIGS. 2A-2B. While the 2D side view 500 of FIG. 5 only illustrates the first rung group 110a, it will be appreciated that each of the other rung groups of the birdcage coil 102 may comprise a substantially similar configuration as described below. Further, for clarity in the 2D side view 500 of FIG. 5, the first conductive ring 104, the second conductive ring 106, and the plurality of conductive rungs 112 of the first rung group 110a are illustrated with a pattern.

As shown in the 2D side view 500 of FIG. 5, the first rung group 110a comprises a first conductive rung 112a, a second conductive rung 112b, a third conductive rung 112e, and a fourth conductive rung 112f. The fourth conductive rung 112f and the first conductive rung 112a are outer conductive rungs of the first rung group 110a. The outer conductive rungs of the first rung group 110a each comprise a plurality of conductive sub-rungs that extend between and are connected to the first conductive ring 104 and the second conductive ring 106. For example, the first conductive rung 112a of the first rung group 110a comprises a plurality of conductive sub-rungs 502 that are connected to and extend between the first conductive ring 104 and the second conductive ring 106. The plurality of conductive sub-rungs 502 comprises a first conductive sub-rung 502a, a second conductive sub-rung 502b, and a third conductive sub-rung 502c. While the 2D side view 500 of FIG. 5 illustrates the plurality of conductive sub-rungs 502 having three (3) conductive sub-rungs, it will be appreciated that the plurality of conductive sub-rungs 502 may comprise any number of conductive sub-rungs (e.g., 2 conductive sub-rungs, 4 conductive sub-rungs, 5 conductive sub-rungs, etc.). In some embodiments, the outer conductive rungs of the first rung group 110a comprises a same number of conductive sub-rungs, as shown in the 2D side view 500 of FIG. 5.

Each of the conductive sub-rungs of a given conductive rung are separated azimuthally from a neighboring conductive sub-rung of the given conductive rung by an azimuth angle 504. For example, the first conductive sub-rung 502a is azimuthally spaced from the second conductive sub-rung 502b by a first azimuth angle 504a, and the second conductive sub-rung 502b is azimuthally spaced from the third conductive sub-rung 502c by a second azimuth angle 504b. In some embodiments, the first azimuth angle 504a is the same as the second azimuth angle 504b. In other embodiments, the first azimuth angle 504a may be different than the second azimuth angle 504b. In further embodiments, the azimuthally spacing between the conductive sub-rungs of the fourth conductive rung 112f of the first rung group 110a mirror the azimuthally spacing between the conductive sub-rungs of the first conductive rung 112a about a centerline of the first rung group 110a. The azimuth angle(s) 504 are less than the azimuth angle(s) 202 between neighboring conductive rungs 112 of the first rung group 110a.

In some embodiments, each of the conductive sub-rungs have a width that is less than the width of the non-edge conductive rungs. For example, the second conductive rung 112b and the third conductive rung 112e have a first width. The first conductive sub-rung 502a has a second width that is less than the first width. The second conductive sub-rung 502b has a third width that is less than the first width. The third conductive sub-rung 502c has a fourth width that is less than the first width. In some embodiments, the second width, the third width, and the fourth width are the same. In other embodiments, one or more of the second width, the third width, and the fourth width are different from one another. In further embodiments, the widths of the conductive sub-rungs of the fourth conductive rung 112f of the first rung group 110a mirror the widths of the conductive sub-rungs of the first conductive rung 112a about the centerline of the first rung group 110a. In some embodiments, each of the conductive sub-rungs have a thickness that is less than the thickness of the non-edge conductive rungs.

Figure 6A:
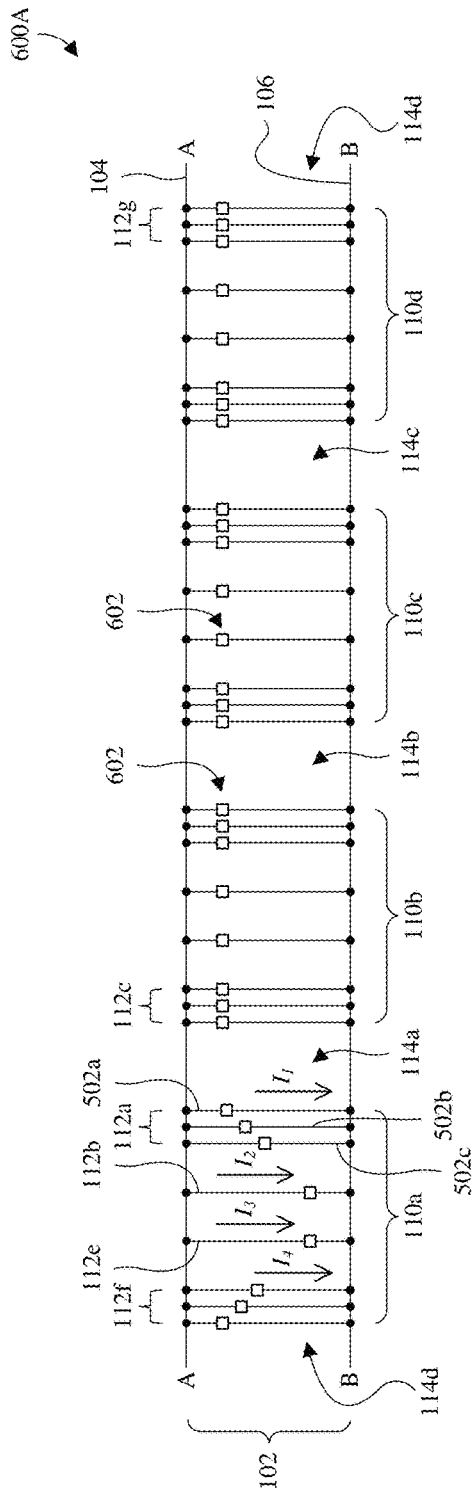
FIGS. 6A-6B illustrates various circuit schematics of some embodiments of the birdcage coil of FIG. 5
Figure 6B:
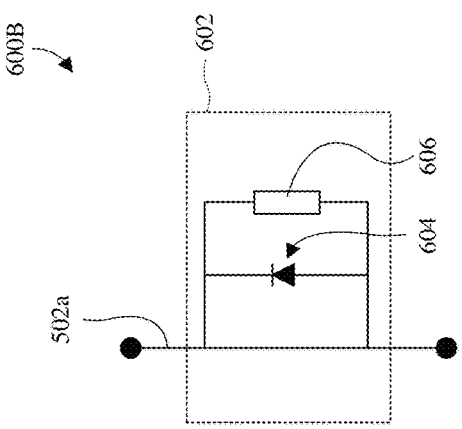

FIGS. 6A-6B illustrates various circuit schematics 600A-600B of some embodiments of the birdcage coil 102 of FIG. 5. More specifically, FIG. 6A illustrates a circuit schematic 600A of an embodiment of the birdcage coil of FIG. 5, and FIG. 6B illustrates a more detailed circuit schematic 600B of some embodiments of a mode switching element 602 of the birdcage coil 102 of FIG. 6A.

As shown in the circuit schematic 600A of FIG. 6A, a first rung group 110a comprises a first conductive rung 112a, a second conductive rung 112b, a third conductive rung 112e, and a fourth conductive rung 112f. The first conductive rung 112a of the first rung group 110a comprises a first plurality of conductive sub-rungs, and the fourth conductive rung 112f of the first rung group 110a comprises a second plurality of conductive sub-rungs. The first plurality of conductive sub-rungs comprises a first conductive sub-rug 502a, a second conductive sub-rung 502b, and a third conductive sub-rung 502c.

The first plurality of conductive sub-rungs are configured to collectively carry a first current $I_1$. The second plurality of conductive sub-rungs are configured to collectively carry a fourth current $I_4$. The second conductive rung 112b is configured to carry a second current $I_2$, and the third conductive rung 112e is configured to carry a third current $I_3$.

Each of the plurality of conductive sub-rungs 502 are configured to carry a percentage of the first current $I_1$. In some embodiments, each of the plurality of conductive sub-rungs 502 are configured to carry about a same percentage of the first current $I_1$. In such embodiments, each of the conductive sub-rungs of a given conductive rung is configured to carry about 1/X of the current the given conductive rung is configured to carry, where X is the total number of conductive sub-rungs of the given conductive rung. For example, the first conductive sub-rung 502a is configured to carry about ⅓ of the first current $I_1$, the second conductive sub-rung 502b is configured to carry about ⅓ of the first current $I_1$, and the third conductive sub-rung 502c is configured to carry about ⅓ of the first current $I_1$.

In some embodiments, various compensation techniques may be utilized to ensure each of the plurality of conductive sub-rungs 502 are configured to carry about a same percentage of the first current $I_1$. For example, the plurality of conductive sub-rungs 502 may have different widths and/or thicknesses than one another. One or more compensation capacitors may be disposed along the first conductive sub-rung 502a, the second conductive sub-rung 502b, and/or the third conductive sub-rung 502c. It will be appreciated that other compensation techniques may be utilized to ensure the plurality of conductive sub-rungs 502 carry about a same percentage of the first current $I_1$.

The current carried by each of the plurality of conductive sub-rungs 502 has a same electrical phase. For example, the current carried by the first conductive sub-rung 502a, the current carried by the second conductive sub-rung 502b, and the current carried by the third conductive sub-rung 502c each have the same electrical phase. In some embodiments, the same electrical phase matches the azimuth angle (from a single reference point) of the first conductive rung 112a.

In some embodiments, the birdcage coil 102 comprises a plurality of mode switching elements 602. The mode switching elements are illustrated as simple block diagrams in the circuit schematic 600A of FIG. 6A for clarity in FIG. 6A. The plurality of mode switching elements 602 allow the birdcage coil 102 to be switched between a transmit mode and a receive mode. The plurality of mode switching elements 602 are disposed along the plurality of conductive rungs 112 and the plurality of conductive sub-rungs 502. For example, a first mode switching element is disposed between a first conductive portion and a second conductive portion of the second conductive rung 112b, a second mode switching element is disposed between a first conductive portion and a second conductive portion of the first conductive sub-rung 502a, a third mode switching element is disposed between a first conductive portion and a second conductive portion of the second conductive sub-rung 502b, and a fourth mode switching element is disposed between a first conductive portion and a second conductive portion of the third conductive sub-rung 502c. In some embodiments, no mode switching elements 602 may be disposed along the first conductive ring 104 or the second conductive ring 106 due to the currents carried by the first conductive ring 104 and the second conductive ring 106 being much higher than the currents carried by the conductive rungs 112.

As shown in the circuit schematic 600B of FIG. 6B, in some embodiments, each of the plurality of mode switching elements 602 comprises a mode switching diode 604 (e.g., a PIN diode). A mode switching control circuit 606 is electrically coupled to the mode switching diode 604. The mode switching control circuit 606 is configured to bias the mode switching diode 604 to activate/deactivate the mode switching diode 604. By activating/deactivating the mode switching diode 604 in each of the plurality of mode switching elements 602, the birdcage coil 102 may be switched between transmit mode and receive mode.

It will be appreciated that the mode switching element 602 illustrated in the circuit schematic 600B of FIG. 6B may comprise other electronic components (e.g., additional diodes, one or more capacitors, one or more inductors, one or more resistors, etc.). It will also be appreciated that the mode switching diode 604 may be some other type of switching device (e.g., a transistor). It will also be appreciated that, while the circuit schematic 600B of FIG. 6B only illustrates the mode switching element 602 on the first conductive sub-rung 502a, each of the plurality of mode switching elements 602 disposed on individual loops and/or elements of the birdcage coil 102 (e.g., other conductive sub-rungs 502 and/or other conductive rungs 112) may have a same (or substantially similar) configuration.

As discussed above, in some embodiments, the conductive edge rungs of each of the rung groups 110 are configured to carry a larger current than non-edge conductive rungs of their respective rung group to compensate for any losses in the $B_1$ field caused by the windows 114. As such, in some embodiments, the first current $I_1$ may be large enough to overload a mode switching element (e.g., the first current $I_1$ may be larger enough to overheat a mode switching diode 604). However, the overloading of the mode switching element may be mitigated by the plurality of sub-rungs.

For example, if the first conductive rung 112a was a single conductive rung and configured to carry 1 ampere (A) of current from the first conductive ring 104 to the second conductive ring 106, the mode switching element (e.g., the mode switching diode 604) disposed along the single conductive rung would receive 1 A. However, by splitting the first conductive rung 112a into two (2) conductive sub-rungs that are configured to carry 0.5 of 1 A, the mode switching elements 602 (e.g., the mode switching diodes 604) disposed along the two (2) conductive sub-rungs will receive 0.5 A (e.g., which is less than 1 A). As such, the overloading issue may be mitigated (e.g., such a configuration may reduce heat on the mode switching diodes by about 75 percent). Accordingly, the conductive sub-rungs 502 may improve reliability and/or performance of the birdcage coil 102.

Figure 7C:
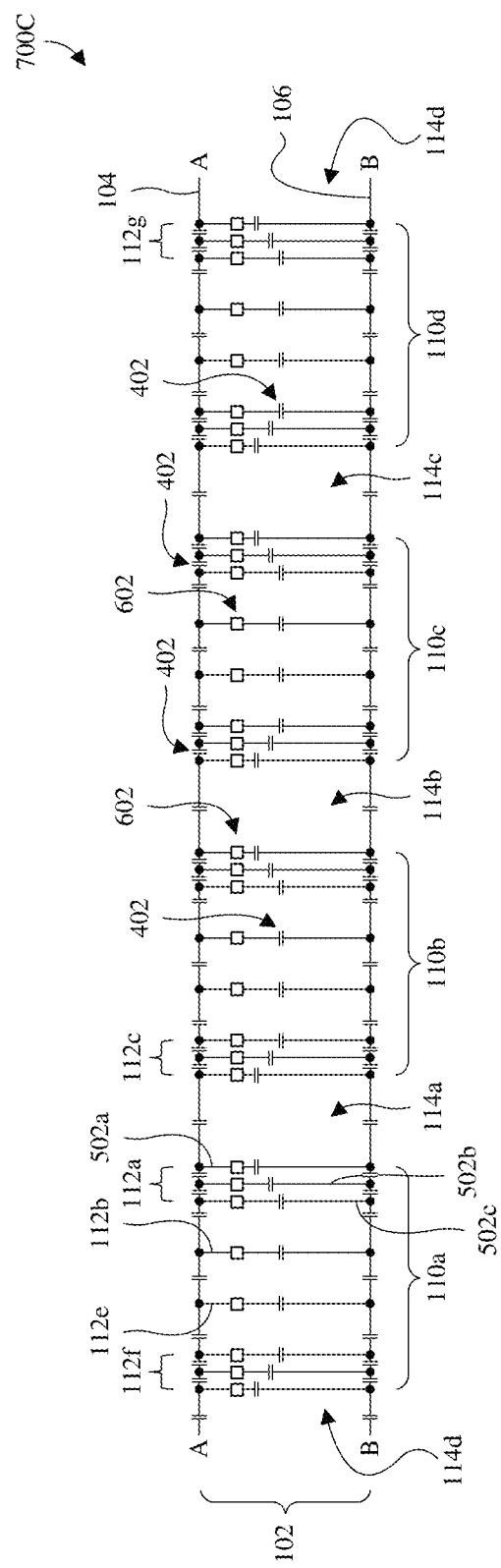

FIGS. 7A-7C illustrate various circuit schematics 700A-700C of some other embodiments of the birdcage coil 102 of FIGS. 2A-2B.

As shown in the various circuit schematics 700A-700C, the birdcage coil 102 may comprise a plurality of capacitors 402 disposed at specific locations on the birdcage coil 102. For example, as shown in the schematic view 700A, the capacitors 402 are disposed along the plurality of conductive rungs 112 and the plurality of conductive sub-rungs 502. For example, a first capacitor is disposed between a first conductive portion and a second conductive portion of the second conductive rung 112b of the first rung group 110a, a second capacitor is disposed between a first conductive portion and a second conductive portion of the first conductive sub-rung 502a, a third capacitor is disposed between a first conductive portion and a second conductive portion of the second conductive sub-rung 502b, and a fourth capacitor is disposed between a first conductive portion and a second conductive portion of the third conductive sub-rung 502c. In such embodiments, the birdcage coil 102 is a low-pass MRI coil.

As shown in the schematic view 700B of FIG. 7B, in other embodiments, the capacitors 402 are disposed along the first conductive ring 104 and the second conductive ring 106 and between both neighboring conductive rungs and neighboring conductive sub-rung. For example, a first capacitor is disposed between a first conductive portion and a second conductive portion of the first conductive ring 104, where the first conductive portion and the second conductive portion of the first conductive ring 104 extend between the first conductive rung 112a and the second conductive rung 112b; a second capacitor is disposed between a third conductive portion and a fourth conductive portion of the first conductive ring 104, where the third conductive portion and the fourth conductive portion extend between the first conductive sub-rung 502a and the second conductive sub-rung 502b; and a third capacitor is disposed between a fifth conductive portion and a sixth conductive portion of the first conductive ring 104, where the fifth conductive portion and the sixth conductive portion extend between the second conductive sub-rung 502b and the third conductive sub-rung 502c. In such embodiments, the birdcage coil 102 is a high-pass MRI coil.

As shown in the schematic view 700C of FIG. 7C, in other embodiments, some of the capacitors 402 are disposed along the first conductive ring 104 and the second conductive ring 106 and between neighboring conductive rungs and neighboring conductive sub-rungs, and some other of the capacitors 402 are disposed along the conductive rungs 112 and along the conductive sub-rungs and between the first conductive ring 104 and the second conductive ring 106. For example, a first capacitor is disposed between a first conductive portion and a second conductive portion of the second conductive rung 112b of the first rung group 110a; a second capacitor is disposed between a first conductive portion and a second conductive portion of the first conductive ring 104, where the first conductive portion and the second conductive portion of the first conductive ring 104 extend between the first conductive rung 112a and the second conductive rung 112b of the first rung group 110a; a third capacitor is disposed between a first conductive portion and a second conductive portion of the second conductive ring 106, where the first conductive portion and the second conductive portion of the second conductive ring 106 extend between the first conductive rung 112a and the second conductive rung 112b of the first rung group 110a; and a fourth capacitor is disposed between a first conductive portion and a second conductive portion of the first conductive sub-rung 502a. In such embodiments, the birdcage coil 102 is a band-pass MRI coil.

Figure 8:
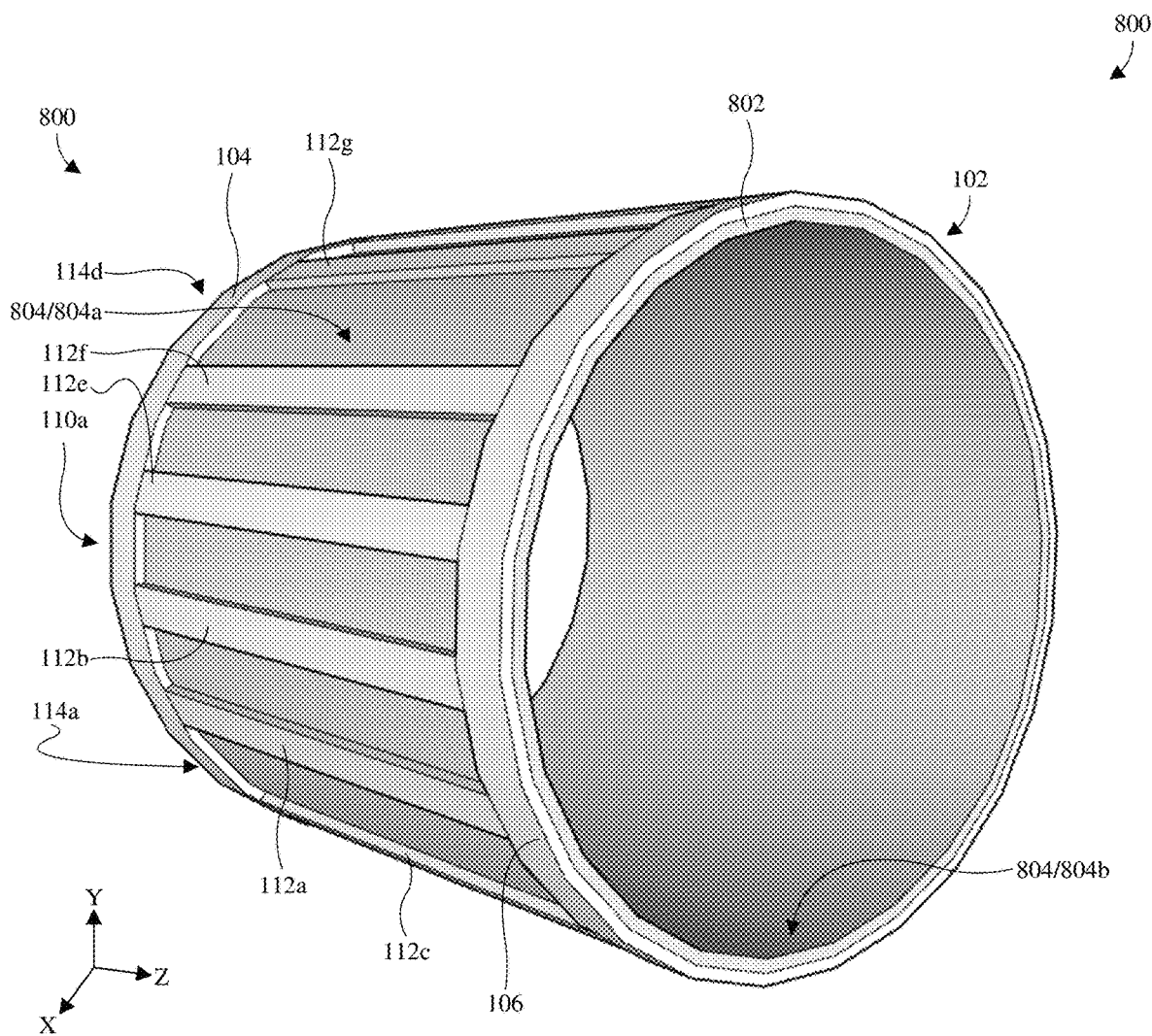
FIG. 8 illustrate a perspective view of some other embodiments of the MRI RF coil of FIGS. 2A-2B.

FIG. 8 illustrate a perspective view 800 of some other embodiments of the MRI RF coil of FIGS. 2A-2B.

The MRI RF coil comprises a birdcage coil 102 that is disposed on a cylindrical-like former 802. The cylindrical-like former 802 has a first surface 804a and a second surface 804b opposite the first surface 804a. The birdcage coil 102 is disposed on the first surface 804 of the cylindrical-like former 802. The first surface 804a and the second surface 804b are separated from one another by a thickness, such that the cylindrical-like former 802 has a tube-like shape. As such, a patient may be placed within the cylindrical-like former 802 and the birdcage coil 102 so that an MR image of the patient may be taken.

In some embodiments, a shape of the cylindrical-like former 802 is such that the cylindrical-like former 802 is a circular cylindrical-like former, as shown in the perspective view 800 of FIG. 8. The cylindrical-like former 802 may be or comprise, for example, plastic, resin, glass fiber, or the like. While the perspective view 800 of FIG. 8 illustrates the former 802 as a solid cylinder, it will be appreciated that the former may comprise multiple individual pieces that may be affixed to one another to form the shape of the cylindrical-like former 802.

FIGS. 9A-9E illustrate various perspective views 900A-900E of some other embodiments of the cylindrical-like former 802 of FIG. 8.

The cylindrical-like former 802 may have a number of different shapes. For example, the cylindrical-like former 802 may have an elliptical cylindrical-like shape, as shown in the perspective view 900A of FIG. 9A. In such embodiments, the cylindrical-like former 802 may be referred to as an elliptical cylindrical-like former.

Figure 9A:
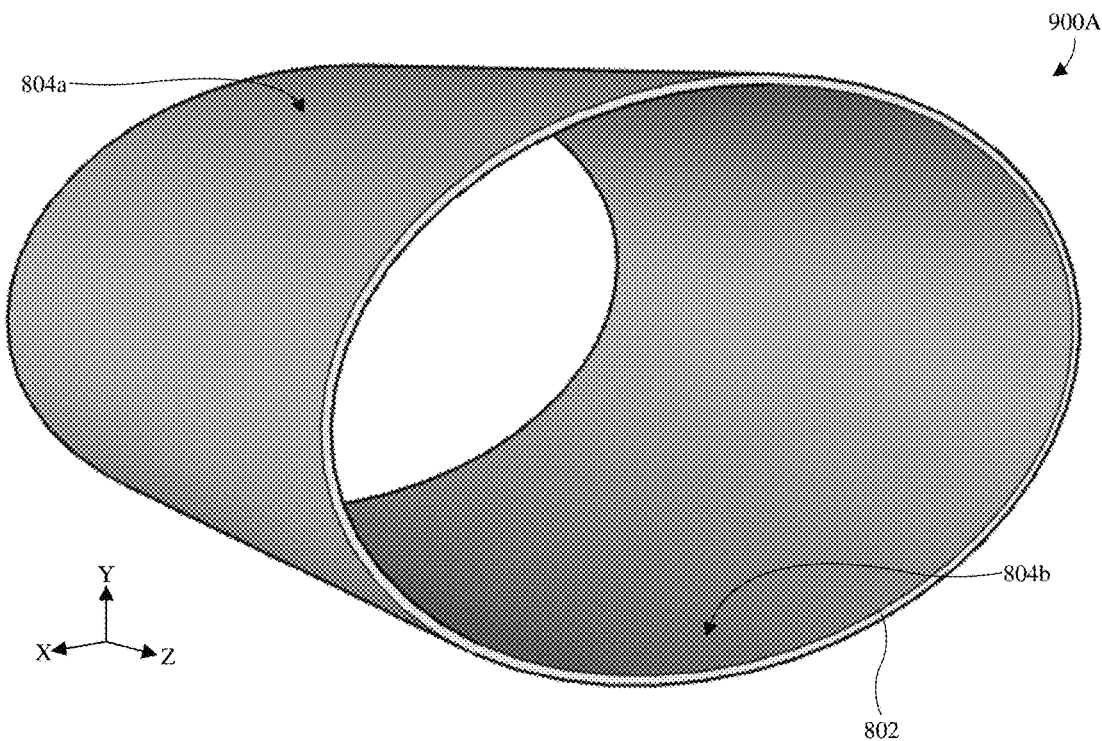
FIGS. 9A-9E illustrate various perspective views of some other embodiments of the cylindrical-like former of FIG. 8.
Figure 9B:
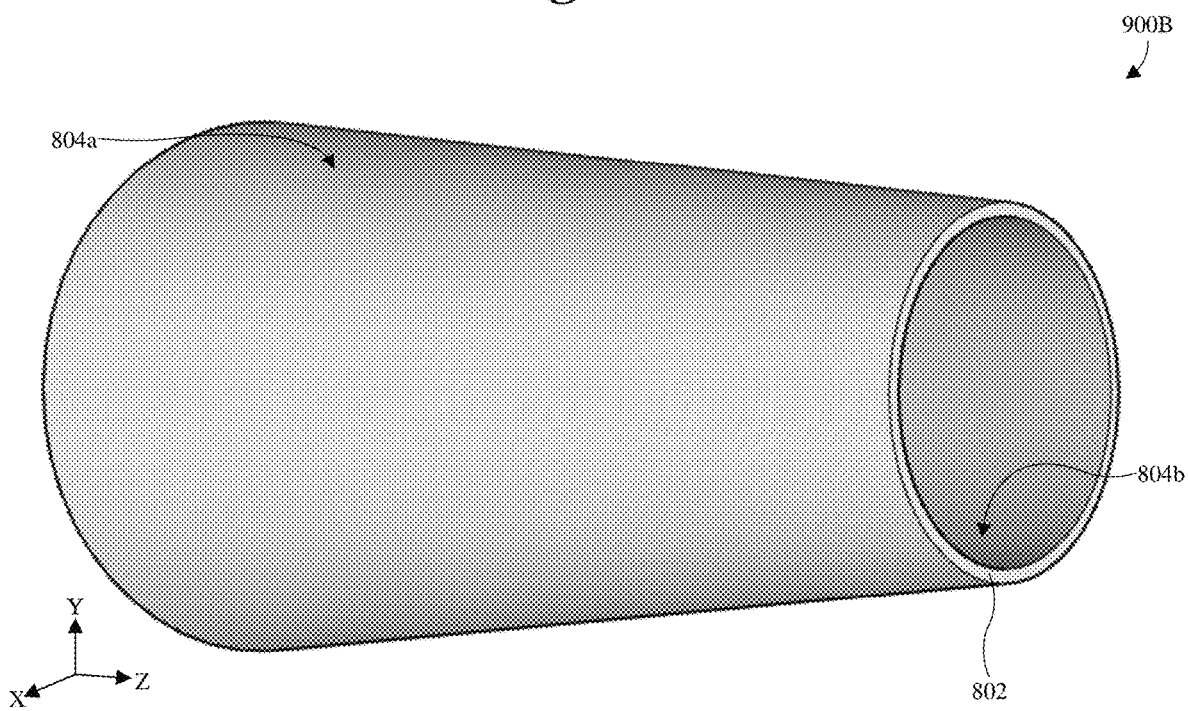

In other embodiments, the cylindrical-like former 802 may have a conical cylindrical-like shape, as shown in the perspective view 900B of FIG. 9B. In such embodiments, the cylindrical-like former 802 may be referred to as a conical cylindrical-like former.

Figure 9C:
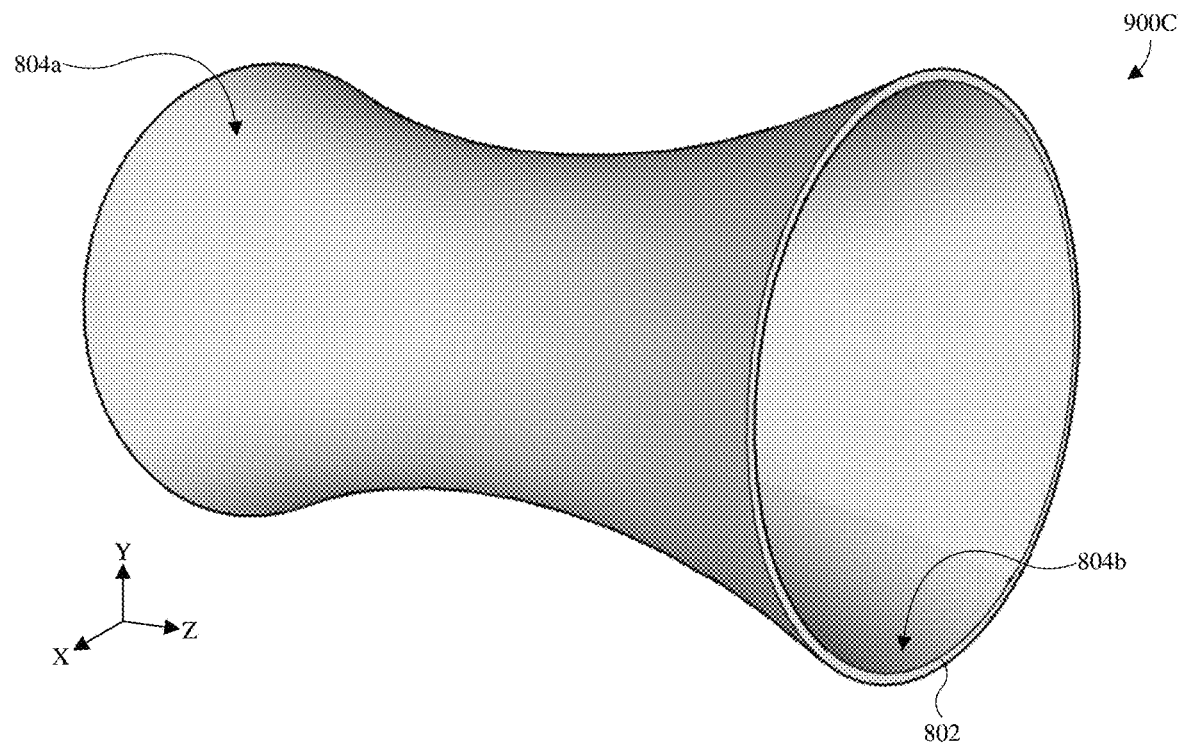

In other embodiments, the cylindrical-like former 802 may have a hyperbolic cylindrical-like shape, as shown in the perspective view 900C of FIG. 9C. In such embodiments, the cylindrical-like former 802 may be referred to as a hyperbolic cylindrical-like former.

Figure 9D:
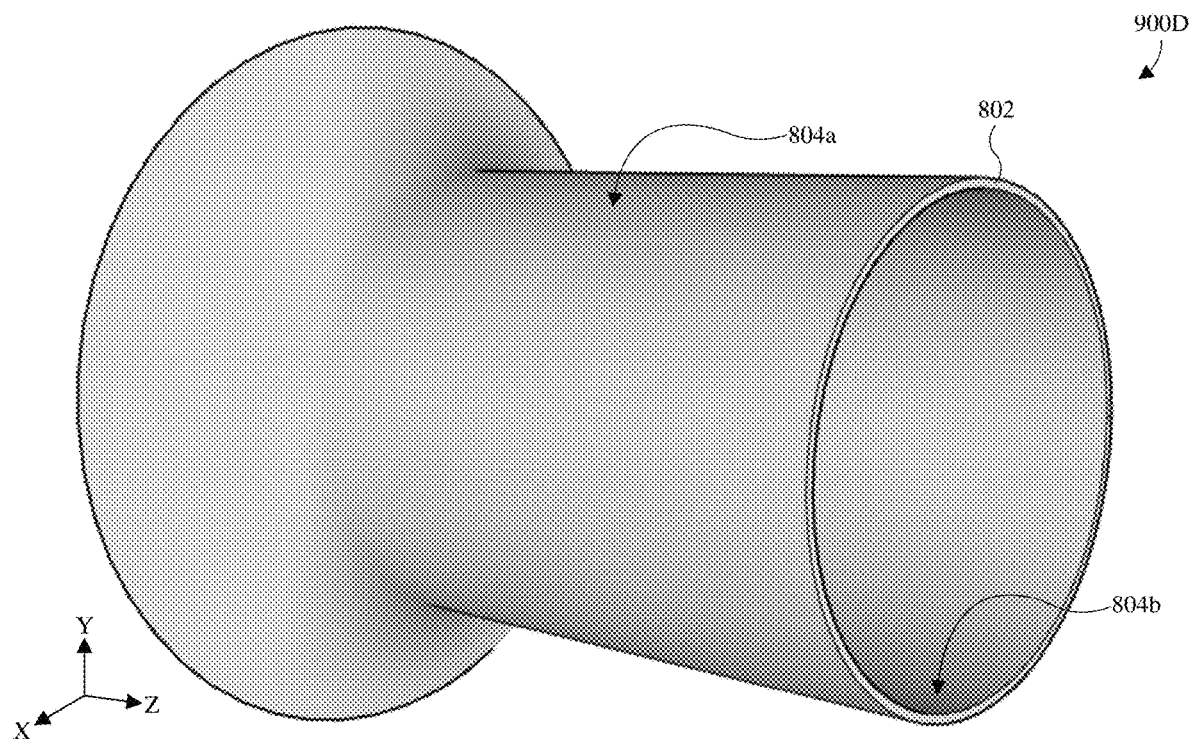

In other embodiments, the cylindrical-like former 802 may have a flared cylindrical-like shape, as shown in the perspective view 900D of FIG. 9D. In such embodiments, the cylindrical-like former 802 may be referred to as a flared cylindrical-like former.

Figure 9E:
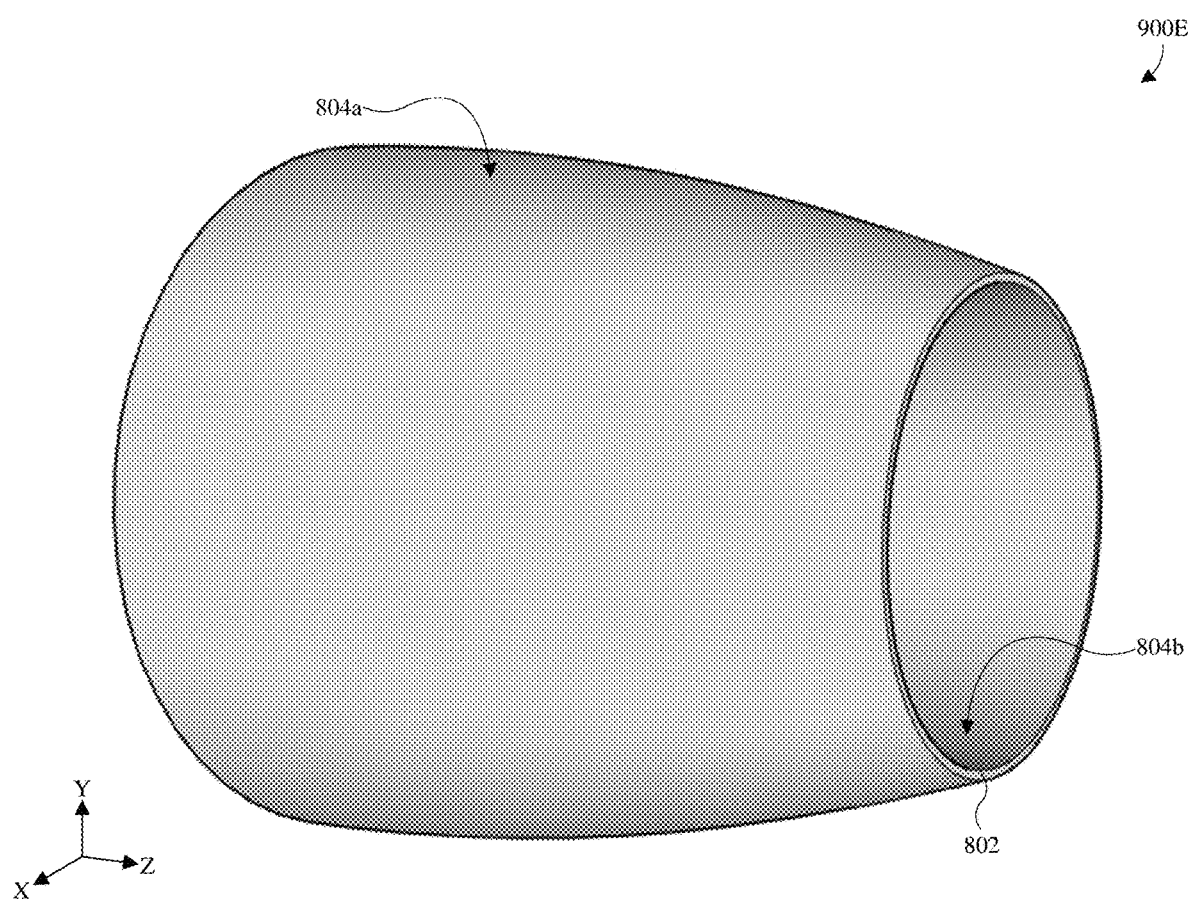

In other embodiments, the cylindrical-like former 802 may have a parabolic cylindrical-like shape, as shown in the perspective view 900E of FIG. 9E. In such embodiments, the cylindrical-like former 802 may be referred to as a parabolic cylindrical-like former.

Figure 10:
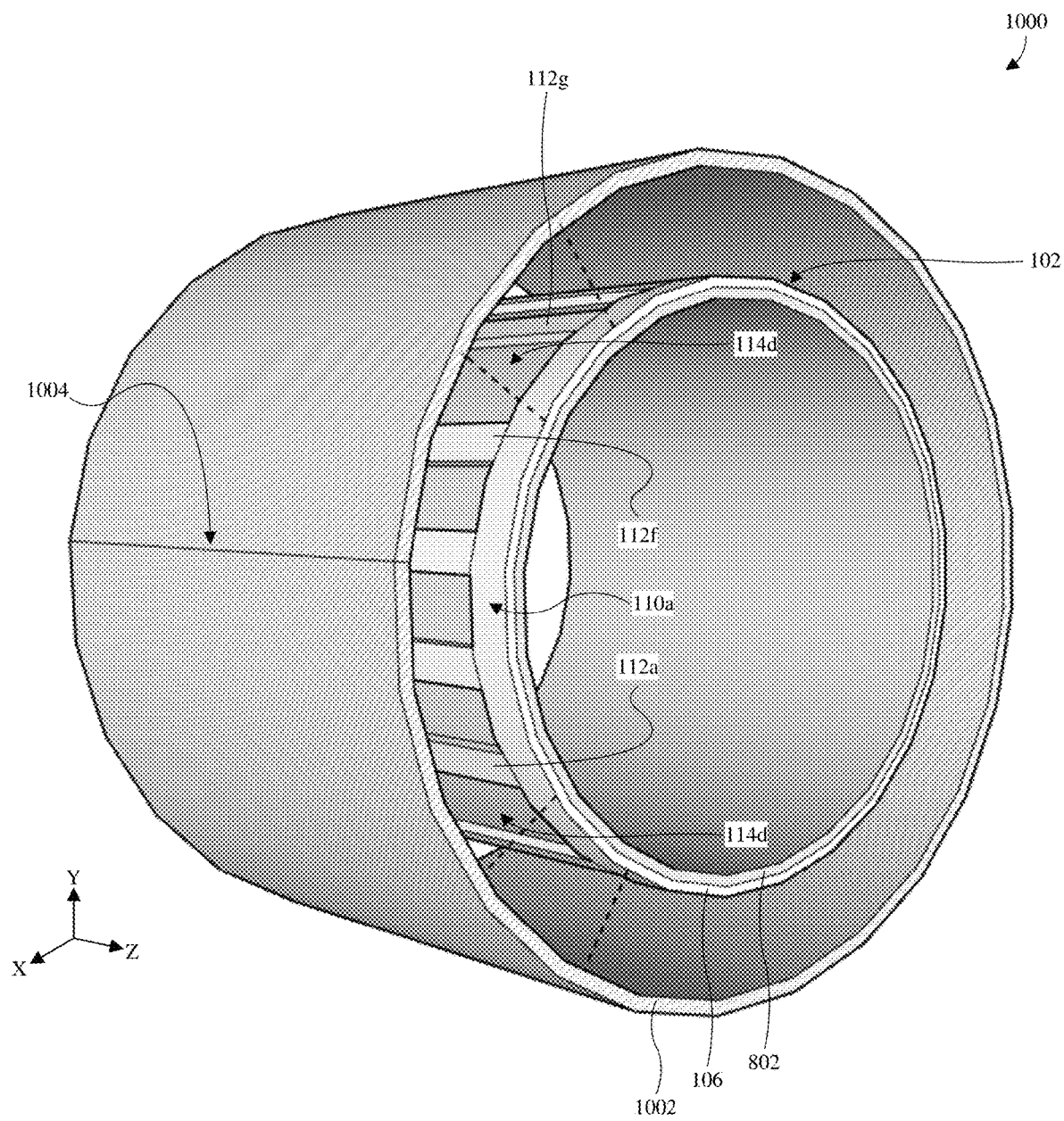
FIG. 10 illustrates a perspective view of some other embodiments of the MRI RF coil of FIGS. 2A-2B.

FIG. 10 illustrates a perspective view 1000 of some other embodiments of the MRI RF coil of FIGS. 2A-2B.

As shown in the perspective view 1000 of FIG. 10, the MRI RF coil comprises a RF shield 1002 surrounding the birdcage coil 102 and the cylindrical-like former 802. The RF shield 1002 is configured to provide decoupling between the birdcage coil 102 and one or more gradient coils and to have a minimized eddy current from a strong gradient pulse. In some embodiments, the RF shield 1002 and the birdcage coil 102 are concentric about an axis.

The RF shield 1002 comprises a conductive material (e.g., a metal). The conductive material has a low conductivity and has a low effect on electromagnetic beams (e.g., a low beam attenuation on radiation and/or x-ray beams that pass through the RF shield 1002). In other words, the RF shield 1002 has low conductivity and low radiation attenuation.

Some examples of a low conductivity material are aluminum and stainless steel. It will be appreciated that other materials are amenable. In some embodiments, a low conductivity material has an electrical conductivity that is less than the electrical conductivity of copper (e.g., $5.96 \times 10^7$ siemens per meter (S/m) at 20° C.).

In some embodiments, a low radiation attenuation material has X-ray mass attenuation coefficients that are less than the X-ray mass attenuation coefficients of stainless steel (e.g., the values of the mass attenuation coefficients, $\mu/\rho$, as a function of photon energy are less in the x-ray range (e.g., photon energy between about 0.0001 megaelectronvolt (MeV) and about 0.1 MeV) than the values of the mass attenuation coefficients as a function of photon energy for stainless steel in the x-ray range). In further embodiments, a low radiation attenuation material has an X-ray mass attenuation coefficient for given photon energy (in the x-ray range) that is less than the X-ray mass attenuation coefficient of stainless steel for the given photon energy. One example of a low radiation attenuation material is aluminum. It will be appreciated that other materials are amenable. Because the RF shield 1002 is a low conductivity and a low radiation attenuation material, an electromagnetic beam (e.g., radiation and/or X-ray beam) may pass through the RF shield 1002 with minimum (or no) beam attenuation (e.g., a small and uniform beam attenuation) and minimized eddy currents (e.g., due to the low conductivity). Accordingly, the RF shield 1002 may further increase the number of new medical modalities that utilize MRI.

In some embodiments, the RF shield 1002 is a low radiation attenuation mesh (e.g., stainless steel mesh, aluminum mesh, copper mesh, etc.). The low radiation attenuation mesh may comprise a low radiation attenuation material (e.g., aluminum) disposed in a mesh (e.g., a plurality of interlaced aluminum structures (e.g., wires), a slotted perforated aluminum sheet, etc.). In some embodiments, the low radiation attenuation mesh may comprise a high radiation attenuation material (e.g., copper) disposed in a mesh. More specifically, in some embodiments, the low radiation attenuation mesh is a slotted perforated copper sheet (e.g., comprising many small slots cut into the copper sheet) that is less than or equal to 8 microns thick. In such embodiments, the slotted perforated copper sheet (with a thickness less than or equal to 8 microns) has a significantly reduced conductivity (e.g., low enough to be comparable to a low radiation attenuation metal), which may reduce eddy currents. In other words, if the slotted perforated copper sheet is greater than 8 microns thick, the conductivity of the slotted perforated copper sheet may be too high, thereby resulting in increased eddy currents. The low radiation attenuation mesh may further reduce beam attenuation (e.g., due to the voids (e.g., air) in the mesh not attenuating the electromagnetic beam) while still having good RF shielding properties, which may further increase the number of new medical modalities that utilize MRI.

The RF shield 1002 comprises one or more joints 1004. The joints 1004 are configured to provide an electrical and mechanical connection between two or more portions of the RF shield 1002. In some embodiments, the joints 1004 comprise a conductive epoxy, solder, or some other conductive material suitable to mechanically and electrically couple together two or more portions of the RF shield 1002. Each of the joints 1004 are disposed directly over a non-windowed areas of the birdcage coil 102. For example, as shown in the perspective view 1000 of FIG. 10, the RF shield 1002 comprise a single joint that is disposed directly over a first rung group 110a of the birdcage coil 102. The first rung group 110a of the birdcage coil 102 is disposed between a first window 114a and a fourth window 114d of the birdcage coil 102 (the dashed lines in FIG. 10 illustrate boundaries of the first window 114a and the fourth window 114d). If an electromagnetic beam were to passes through the RF shield 1002 at or near the joints 1004, the joints 1004 may cause large and/or uneven disturbances in the electromagnetic beam (e.g., due to manufacturing tolerances, material properties, etc.). Accordingly, because the joints 1004 are disposed directly over the non-windowed areas of the birdcage coil 102, beam attenuation by the RF shield 1002 may be minimized (e.g., because the windows are configured to be radiation beam-through areas), which may further increase the number of new medical modalities that utilize MRI.

Figure 11:
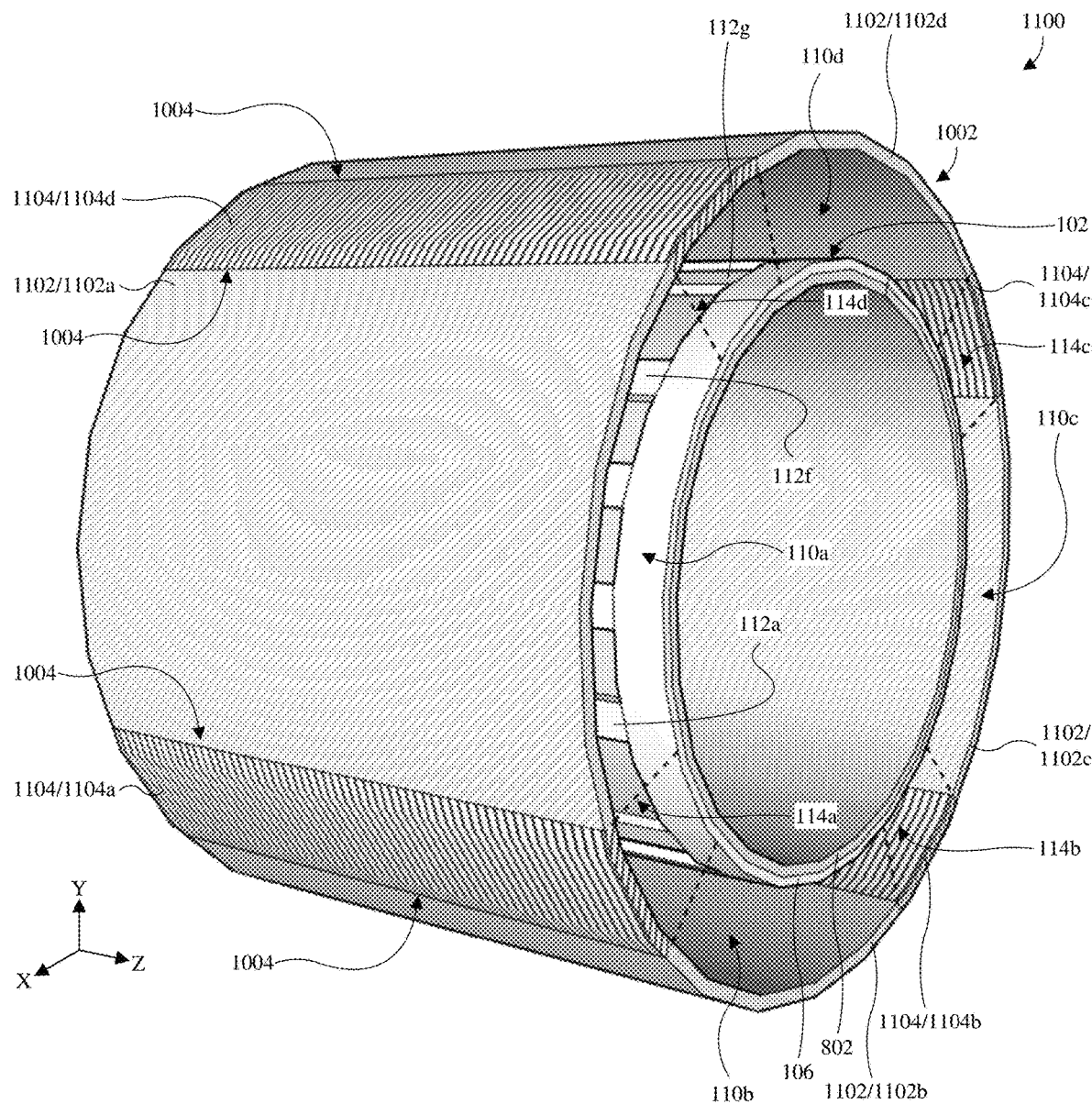
FIG. 11 illustrates a perspective view of some other embodiments of the MRI RF coil of FIGS. 2A-2B.

FIG. 11 illustrates a perspective view 1100 of some other embodiments of the MRI RF coil of FIGS. 2A-2B.

As shown in the perspective view 1100 of FIG. 11, the RF shield comprises 1002 comprises a plurality of high radiation attenuation material portions 1102 and a plurality of low radiation attenuation material portions 1104. The plurality of high radiation attenuation material portions 1102 are disposed directly over the non-windows areas of the birdcage coil 102, respectively. For example, a first high radiation attenuation material portion 1102a is disposed directly over a first rung group 110a of the birdcage coil 102, a second high radiation attenuation material portion 1102b is disposed directly over a second rung group 110b of the birdcage coil 102, a third high radiation attenuation material portion 1102c is disposed directly over a third rung group 110c of the birdcage coil 102, and a fourth high radiation attenuation material portion 1102d is disposed directly over a fourth rung group 110d of the birdcage coil 102. The plurality of low radiation attenuation material portions 1104 are disposed directly over a plurality of windows 114 of the birdcage coil 102, respectively. For example, a first low radiation attenuation material portion 1104a is disposed directly over a first window 114a of the birdcage coil 102, a second low radiation attenuation material portion 1104b is disposed directly over a second window 114b of the birdcage coil 102, a third low radiation attenuation material portion 1104c is disposed directly over a third window 114c of the birdcage coil 102, and a fourth low radiation attenuation material portion 1104d is disposed directly over a fourth window 114d of the birdcage coil 102. The plurality of high radiation attenuation material portions 1102 and the plurality of low radiation attenuation material portions 1104 are joined together (mechanically and electrically) via joints 1004 that are disposed directly over the interface in which non-windowed areas of the birdcage coil 102 meet the windows 114 of the birdcage coil 102.

The plurality of high radiation attenuation material portions 1102 comprise a first conductive material (e.g., a first metal). The first conductive material has a relatively high effect on electromagnetic beams (e.g., a high beam attenuation on radiation and/or x-ray beams that pass through the first conductive material). For example, in some embodiments, the first conductive material has X-ray mass attenuation coefficients that are equal to or greater than the X-ray mass attenuation coefficients of stainless steel (e.g., the values of the mass attenuation coefficients as a function of photon energy in the x-ray range are greater than or equal to the values of the mass attenuation coefficients as a function of photon energy for stainless steel in the x-ray range). In further embodiments, the first conductive material has an X-ray mass attenuation coefficient for given photon energy (in the x-ray range) that is greater than or equal to the X-ray mass attenuation coefficient of stainless steel for the given photon energy. Some examples of the first conductive material are copper, stainless steel, or the like. It will be appreciated other materials are amenable.

The plurality of low radiation attenuation material portions 1104 comprise a second conductive material (e.g., a second metal). The second conductive material has a relatively low effect on the electromagnetic beams (e.g., a low beam attenuation on radiation and/or x-ray beams that pass through the second conductive material). For example, in some embodiments, the second conductive material has X-ray mass attenuation coefficients in the x-ray range that are less than the X-ray mass attenuation coefficients of stainless in the x-ray range. In further embodiments, the second conductive material has an X-ray mass attenuation coefficient for given photon energy (in the x-ray range) that is less than the X-ray mass attenuation coefficient of stainless steel for the given photon energy. One example of a low radiation attenuation material are aluminum. It will be appreciated other materials are amenable.

In some embodiments in which the RF shield 1002 comprises the plurality of high radiation attenuation material portions 1102 and the plurality of low radiation attenuation material portions 1104, the RF shield may be referred to as a hybrid RF shield. Because the RF shield 1002 comprises both the plurality of high radiation attenuation material portions 1102 and the plurality of low radiation attenuation material portions 1104, the RF shield 1002 may have increased decoupling properties while also having low beam attenuation. Accordingly, the hybrid RF shield may further increase the number of new medical modalities that utilize MRI.

In some embodiments, the first conductive material is disposed in a mesh (e.g., stainless steel mesh), and the second conductive material is disposed in a mesh (e.g., stainless steel mesh, aluminum mesh, copper mesh, etc.). In such embodiments, the second conductive material mesh has a higher X-ray mass attenuation coefficient than the first conductive material mesh. In further embodiments, the plurality of high radiation attenuation material portions 1102 may be non-mesh structures (e.g., copper sheets, stainless steel sheets, etc.), and the plurality of low radiation attenuation material portions 1104 are mesh structures (e.g., aluminum mesh, copper mesh, etc.).

In some embodiments, the X-ray mass attenuation coefficient of the first conductive material is greater than a threshold value. In further embodiments, the X-ray mass attenuation coefficient of the second conductive material is less than or equal to the threshold value. In other words, the low radiation attenuation material is less than or equal to the threshold value and the high radiation material is greater than the threshold value. In yet further embodiments, the threshold value may be 1 percent (e.g., the low radiation material may only reduce the electromagnetic beam by less than or equal to 1 percent). It will be appreciated that, in such embodiments, the second conductive material may be any material that satisfies the threshold value (1 percent).

Figure 12:
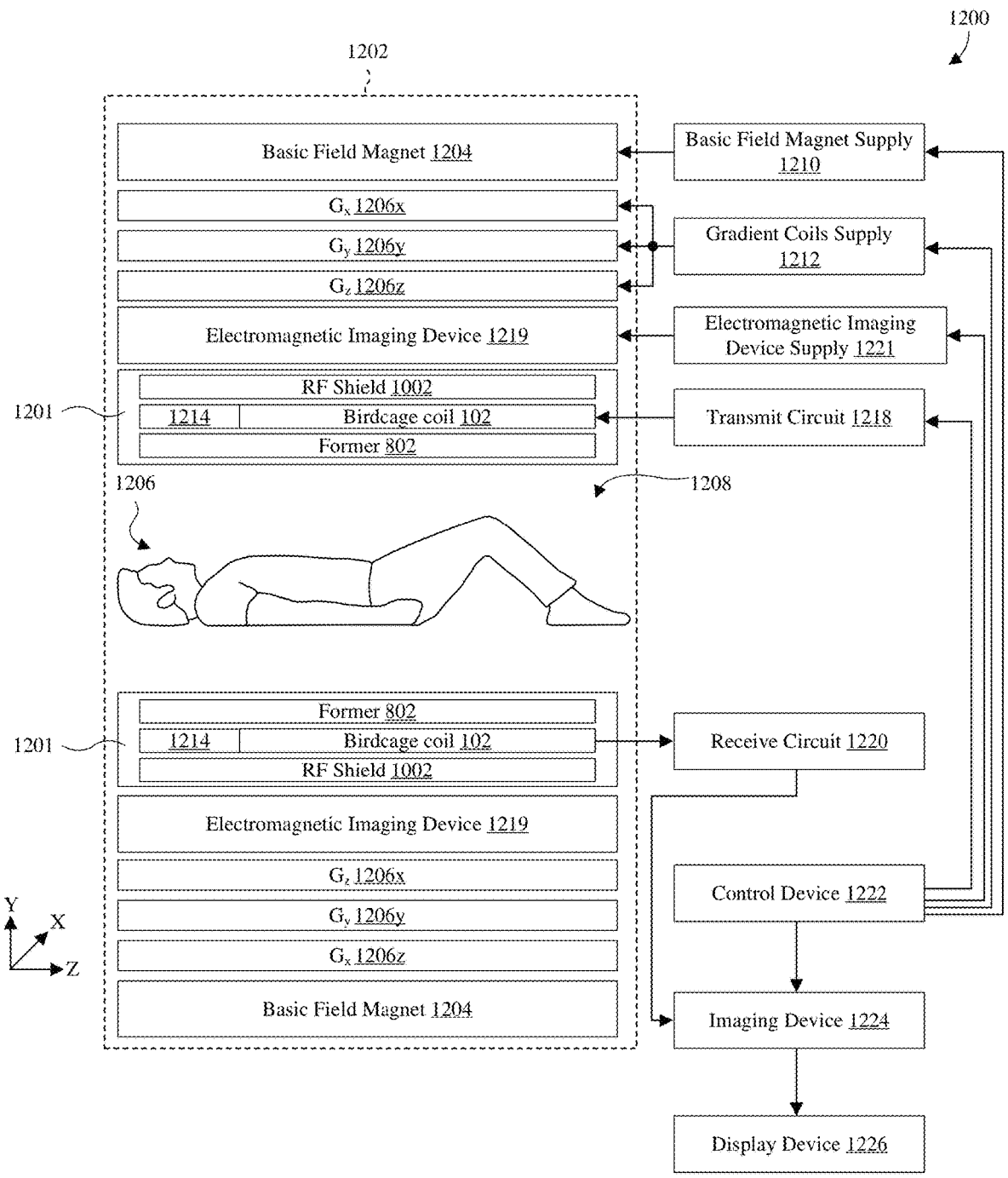
FIG. 12 illustrates a block diagram of some embodiments of an MRI system comprising a MRI RF coil that has a birdcage coil having a plurality of windows and a plurality of rung groups.

FIG. 12 illustrates a block diagram 1200 of some embodiments of an MRI system comprising a MRI RF coil 1201 that has a birdcage coil 102 having a plurality of windows and a plurality of rung groups. The MRI RF coil may, for example, be as in any one or combination of FIGS. 1, 2A-2B, 3, 4A-4C, 5, 6, 7A-7C, 8, 9A-9E, 10, and 11.

The MRI system comprises a scanner 1202. The scanner 1202 comprises a basic field magnet 1204, a plurality of gradient coils 1206x-1206z, and a MRI RF coil 1201. In some embodiments, the MRI RF coil is a system built-in transmit/receive coil-whole body coil (WBC) for MRI systems from low field to high field, such as 0.7 tesla (T), 1.5 T, 3 T, etc.

The basic field magnet 1204, the gradient coils 1206x-1206z, and the MRI RF coil 1201 are arranged around a bore 1208 of the scanner 1202, which receives a patient 1206. The basic field magnet 1204 is electrically coupled to, and controlled in part by, a basic field magnet power supply 1210. The basic field magnet 1204 produces a $B_0$ magnetic field over the patient 1206 (e.g., within the bore 1208). In some embodiments, the $B_0$ magnetic field strength is 0.7 T, 1.5 T, 3.0 T, or some other suitable $B_0$ magnetic field strength.

The plurality of gradient coils 1206x-1206z emit gradient magnetic fields to spatially encode MRI signals received from the patient 1206. The plurality of gradient coils 1206x-1206z include an x-direction gradient coil 1206x, a y-direction gradient coil 1206y, and a z-direction gradient coil 1206z for spatially encoding the MRI signals respectively in the X direction, the Y direction, and the Z direction. The Z direction is parallel to the $B_0$ magnetic field produced by the basic field magnet 1204, whereas the X and Y directions are transverse to the $B_0$ magnetic field. In alternative embodiments, one or more of the gradient coils 1206x-1206z is/are omitted. The gradient coils 1206x-1206z are electrically coupled to, and controlled in part by, a gradient coil power supply 1212.

The MRI RF coil 1201 comprises a cylindrical-like former 802, a birdcage coil 102, and an RF shield 1002. The birdcage coil 102 has a plurality of windows and a plurality of rung groups. The birdcage coil 102 is disposed on the cylindrical-like former 802. The RF shield 1002 surrounds both the birdcage coil 102 and the cylindrical-like former 802. In some embodiments, the birdcage coil 102 comprises or is otherwise associated with a control circuit 1214. The control circuit 1214 is configured to switch the birdcage coil 102 between transmit mode and receive mode. For example, the control circuit 1214 provides signals (e., electrical signals) to a plurality of mode switching elements 602 (see, e.g., FIGS. 6A-6B) that, in response to receiving the signals, either activate or deactivate the mode switching diodes 604 (see, e.g., FIGS. 6A-6B), thereby switching the birdcage coil between transmit mode and receive mode. It will be appreciated that, in some embodiments, the MRI RF coil 1201 is only configured to operate in the transmit mode. In such embodiments, it will be appreciated that a second coil (e.g., a knee coil, head coil, etc.) configured to operate in receive mode may be placed with the patient 1206 inside the bore 1208. In further such embodiments, the control circuit 1214 may be configured to deactivate (e.g., disable) the birdcage coil 102 during receive mode.

A transmit circuit 1218 and a receive circuit 1220 are electrically coupled to the birdcage coil 102. The transmit circuit 1218 is electrically coupled to and drives the birdcage coil 102 to generate a $B_1$ magnetic field transverse to the $B_0$ magnetic field when the MRI system operates in transmit mode. For example, the transmit circuit 1218 may drive the birdcage coil 102 to generate radiofrequency (RF) pulses at the Larmor frequency. The transmit circuit 1218 is configured to provide an alternating current (AC) to the birdcage coil 102 so that the birdcage coil 102 generates the $B_1$ magnetic field (e.g., the birdcage coil 102 outputs the $B_1$ field in response to receiving the AC current). It will be appreciated that, in some embodiments, the transmit circuit 1218 provides signals to a transmit circuit power supply (not shown) that then provides the AC current to the birdcage coil 102. The $B_1$ magnetic field excites protons in the patient 1206, which causes the protons to emit MRI signals. The receive circuit 1220 is electrically coupled to the birdcage coil 102 and receives the MRI signals in response to excitation of the protons by the birdcage coil 102. In some embodiments, the transmit circuit 1218 and/or the receive circuit 1220 are disposed in the scanner 1202 (e.g., in a housing of the scanner 1202). In other embodiments, the transmit circuit 1218 and/or the receive circuit 1220 are disposed outside the scanner 1202.

In some embodiments, the scanner 1202 comprises an electromagnetic imaging device 1219. The electromagnetic imaging device 1219 is electrically coupled to, and controlled in part, by an electromagnetic imaging device power supply 1221. The electromagnetic imaging device 1219 is configured to take an image of the patient 1206 by utilizing electromagnetic beams (e.g., radiation and/or X-ray beams). For example, in some embodiments, the electromagnetic imaging device 1219 is an X-ray machine that comprises an X-ray generator and an X-ray detector. The X-ray generator is configured to generate X-ray that are directed through the windows on the birdcage coil 102 to the patient 1206. The X-ray detector is configured to receive X-ray signals in response to the X-rays, so that an X-ray image of the patient 1206 may be generated.

The basic field magnet power supply 1210, the gradient coil power supply 1212, the transmit circuit 1218, the electromagnetic imaging device power supply 1221, or any combination of the foregoing is/are controlled by a control device 1222. For example, the control device 1222 provides signals to the transmit circuit 1218 so that the transmit circuit 1218 drives the birdcage coil 102 to generate the $B_1$ magnetic field. In some embodiments, the control device 1222 is disposed within the scanner 1202 (e.g., housing of the scanner 1202). In other embodiments, the control device 1222 is disposed outside the scanner 1202. In some embodiments, some other coil (not shown) (e.g., a knee receive coil) may be inductively coupled (e.g., via the MRI RF coil 1201) or directly coupled (e.g., via a physical connection, such as one or more conductive wires) to the scanner 1202.

An imaging device 1224 receives MRI signals from the receive circuit 1220 and, in some embodiments, receives control signals from the control device 1222. Based thereon, the imaging device 1224 generates an MR image of the patient 1206 and outputs the MR image to a display device 1226. The imaging device 1224 generates the MR image by performing a transformation process on the MRI signals, such as, for example, a two-dimensional fast Fourier transform (FFT) or some other suitable transform. While not shown, it will be appreciated that imaging device 1224 may also (or the electromagnetic imaging device may directly) generate an electromagnetic beam based image of the patient 1206 and output the electromagnetic beam based image to the display device 1226.

The control device 1222 may, for example, be a general-purpose device (e.g., a computer) executing instructions or an application-specific device. Similarly, the imaging device 1224 may, for example, be a general-purpose device (e.g., a computer) executing instructions or an application-specific device. While the control device 1222 and the imaging device 1224 are shown as being separate, the control device 1222 and the imaging device 1224 may be integrated together in alternative embodiments.

While the block diagram 1200 of FIG. 12 illustrates the MRI RF coil 1202 as a transmit/receive WBC, the MRI RF coil may be a Tx-only coil (e.g., configured to operate only in a transmit mode) or a Rx-only coil (e.g., configured to operate only in a receive mode). It will also be appreciated that the MRI RF coil may be other types of MRI coils (e.g., a knee coil, a head coil, etc.).

Figure 13:
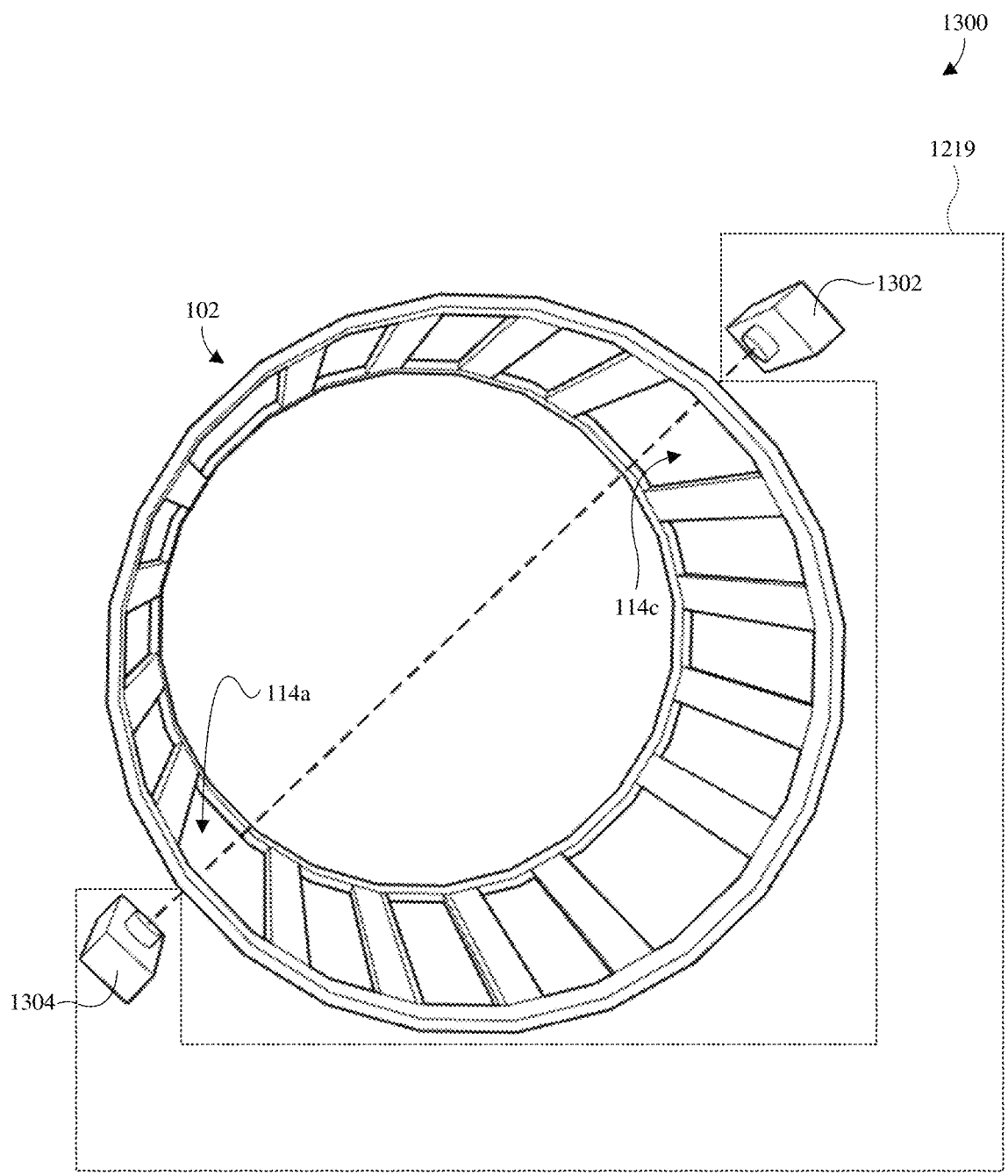
FIG. 13 illustrates a simplified perspective view of some embodiments of the MRI system of FIG. 12.

FIG. 13 illustrates a simplified perspective view 1300 of some embodiments of the MRI system of FIG. 12. The simplified perspective view 1300 of FIG. 13 is "simplified" because the simplified perspective view 1300 of FIG. 13 only illustrates the birdcage coil 102 and the electromagnetic imaging device 1219 of the MRI system.

As shown in the simplified perspective view 1300 of FIG. 13, the electromagnetic imaging device 1219 comprises an electromagnetic beam generator 1302 and an electromagnetic beam detector 1304. For example, in some embodiments, the electromagnetic imaging device 1219 is an X-ray system configured to generate an X-ray image of a patient 1206 (see, e.g., FIG. 12). In such embodiments, the electromagnetic beam generator 1302 is an X-ray generator and the electromagnetic beam detector 1304 is an X-ray detector. It will be appreciated that other types of electromagnetic imaging devices (or other types of electromagnetic systems) are amenable (e.g., radiation therapy systems, computed tomography (CT) systems, tomosynthesis systems, or the like). It will also be appreciated that such other types of electromagnetic imaging devices comprise one or more electromagnetic beam generators and/or one or more electromagnetic beam detectors that are suitable for their given electromagnetic device type.

Also shown in the simplified perspective view 1300 of FIG. 13, the electromagnetic beam generator 1302 is positioned such that an electromagnetic beam generated by the electromagnetic beam generator 1302 passes through one of the plurality of windows 114 of the birdcage coil 102 on its way toward the patient 1206. For example, the electromagnetic beam generator 1302 may generate an electromagnetic that passes through a third window 114c of the birdcage coil 102 on its way to the patient 1206. In other words, the electromagnetic beam generator 1302 is disposed directly over the third window 114c of the birdcage coil 102.

The electromagnetic beam detector 1304 is positioned such that the electromagnetic beam detector 1304 is configured to receive imaging signals (in response to the electromagnetic beam) that pass through one or more of the windows 114. For example, the electromagnetic beam detector 1304 is configured to receive imaging signals from the patient 1206 that pass through a first window 114a of the birdcage coil 102. In other words, the electromagnetic beam detector 1304 is disposed directly over the first window 114a of the birdcage coil 102. Note that the dashed line extending between the electromagnetic beam generator 1302 and the electromagnetic beam detector 1304 is a straight line that is included to better illustrate the positioning of the electromagnetic beam generator 1302 and the electromagnetic beam detector 1304 in relation to the windows 114 of the birdcage coil 102.

In some embodiments, the electromagnetic beam generator 1302 and the electromagnetic beam detector 1304 are azimuthally separated by 180 degrees, as shown in the simplified perspective view 1300 of FIG. 13. It will be appreciated that the electromagnetic beam generator 1302 and the electromagnetic beam detector 1304 may be azimuthally separated by some other azimuth (e.g., 90 degrees, 270 degrees, etc.). It will also be appreciated that the MRI system may comprise more than one electromagnetic beam generator 1302 and/or more than one electromagnetic beam detector 1304. In such embodiments, each of the electromagnetic beam generators 1302 and each of the electromagnetic beam detectors 1304 are positioned in such a way as to be disposed directly over one of the windows 114 of the birdcage coil 102.

Figure 14:
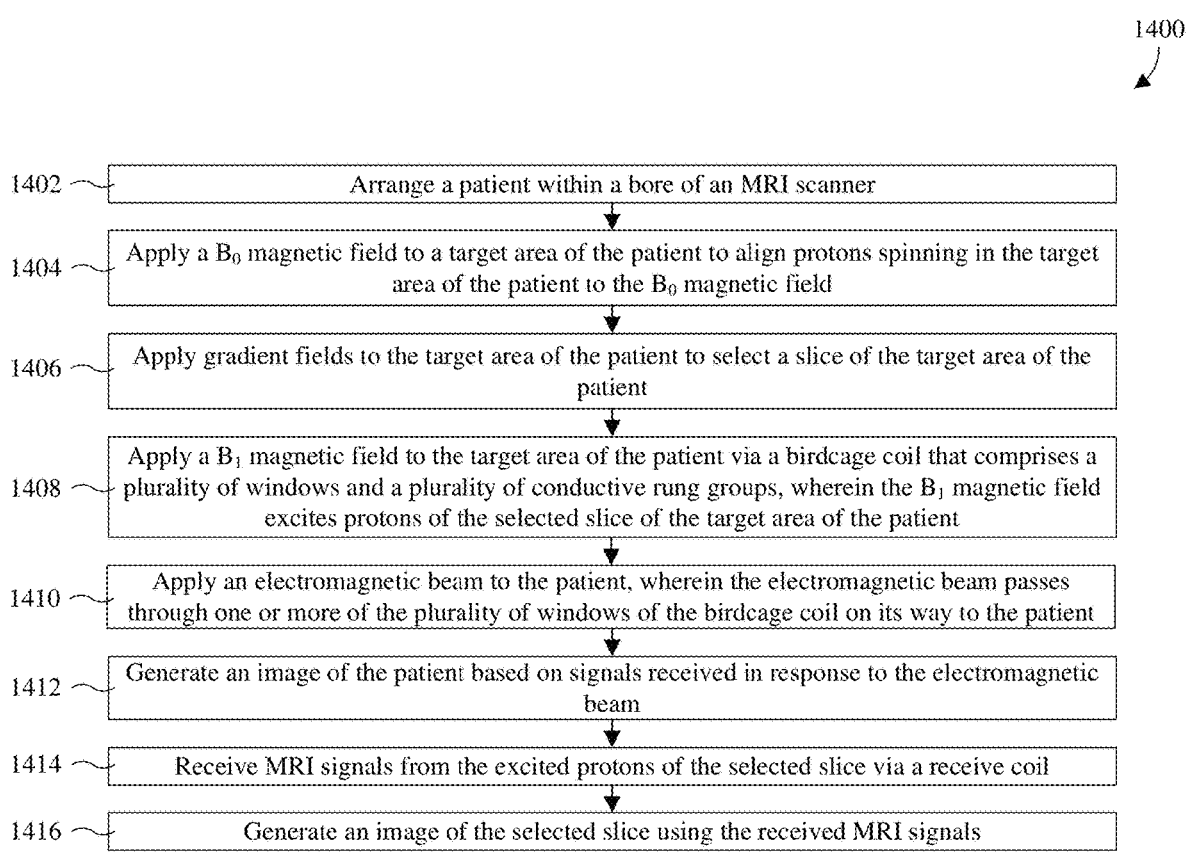
FIG. 14 illustrates a flowchart of a method for performing an MRI process using a MRI RF coil comprising a birdcage coil that has a plurality of windows and a plurality of rung groups.

FIG. 14 illustrates a flowchart 1400 of a method for performing an MRI process using a MRI RF coil comprising a birdcage coil 102 that has a plurality of windows and a plurality of rung groups. The MRI RF coil may, for example, be as in any one or combination of FIGS. 1, 2A-2B, 3, 4A-4C, 5, 6, 7A-7C, 8, 9A-9E, 10, 11, and 13. Further, the MRI process may, for example, be performed by the MRI system of FIG. 12, FIG. 13, or some other suitable MRI system.

While the flowchart 1400 of FIG. 14 is illustrated and described herein as a series of acts or events, it will be appreciated that the illustrated ordering of such acts or events is not to be interpreted in a limiting sense. For example, some acts may occur in different orders and/or concurrently with other acts or events apart from those illustrated and/or described herein. Further, not all illustrated acts may be required to implement one or more aspects or embodiments of the description herein, and one or more of the acts depicted herein may be carried out in one or more separate acts and/or phases.

At 1402, a patient is arranged within a bore of an MRI scanner. For example, the patient and a MRI knee coil are moved into a bore of the MRI scanner on a slide table. See, for example, the scanner 1202 of FIG. 12.

At 1404, a $B_0$ magnetic field is applied to a target area (e.g., a knee, the head, etc.) of the patient to align protons spinning in the target area of the patient to the $B_0$ magnetic field. The $B_0$ magnetic field may, for example, be applied by the basic field magnet 1204 of FIG. 12 and the basic field magnet power supply 1210 of FIG. 12.

At 1406, gradient fields are applied to the target area of the patient to select a slice of the target area of the patient (e.g., a slice of the patient's knee). The gradient fields may, for example, be applied by the gradient coils 1206x-1206z of FIG. 12 and the gradient coil power supply 1212 of FIG. 12.

At 1408, a $B_1$ magnetic field is applied to the target area of the patient via a birdcage coil that comprises a plurality of windows and a plurality of conductive groups, wherein the $B_1$ magnetic field excites protons of the selected slice of the target area of the patient. The birdcage coil may, for example, be as in any one or combination of FIGS. 1, 2A-2B, 3, 4A-4C, 5, 6, 7A-7C, 8, 9A-9E, 10, and 11.

At 1410, an electromagnetic beam is applied to the patient, wherein the electromagnetic beam passes through one or more of the plurality of windows of the birdcage coil as it travels (e.g., propagates) toward the patient. The electromagnetic beam may be applied to the patient by, for example, the electromagnetic imaging device 1219 of FIG. 12. More specifically, in some embodiments, the electromagnetic beam may be applied to the patient by the electromagnetic beam generator 1302 of FIG. 13. The electromagnetic beam may be applied at any time (e.g., before/after the $B_0$ field is applied, before/after the $B_1$ field is applied, interleaved between RF pulses of an MRI scan, etc.). In some embodiments, the electromagnetic beam is an X-ray beam that is generated by an X-ray generator.

At 1412, an image of the patient is generated based on signals received in response to the electromagnetic beam. This image may be generated at any time (e.g., before/after the $B_0$ field is applied, before/after the $B_1$ field is applied, etc.). The signals may be received (e.g., detected) by, for example, the electromagnetic imaging device 1219 of FIG. 12. More specifically, in some embodiments, the signals may be received (e.g., detected) by the electromagnetic beam detector 1304 of FIG. 13. For example, in some embodiments, the received signals are X-ray signals detected by an X-ray detector, which are used to generate an X-ray image of the patient.

At 1414, MRI signals are received from the excited protons of the selected slice via a receive coil. The MRI signals may, for example, be received by the birdcage coil 102 and the receive circuit 1220 of FIG. 12. In other embodiments, a different coil (e.g., a head coil, shoulder coil, etc.) may receive the MRI signals. The MRI signals may be received at any time in relation to applying the electromagnetic to the patient and/or receiving the signals in response to the electromagnetic beam (e.g., before/after the electromagnetic beam is applied to the patient, before/after the signals are received in response to the electromagnetic beam, interleaved between applying the electromagnetic beam to the patient and receiving the signals in response to the electromagnetic beam).

At 1416, an image of the selected slice is generated using the received MRI signals. The image may, for example, be generated by the imaging device 1224 of FIG. 12 and/or may, for example, be displayed on the display device 1226 of FIG. 12.

In view of the foregoing, some embodiments of the present disclosure provide a MRI RF coil configured to operate in at least one of a transmit (Tx) mode or a receive (Rx) mode. The MRI RF coil comprises a first conductive ring; a second conductive ring is spaced from the first conductive ring; a plurality of rung groups extend between the first and second conductive rings, wherein: the plurality of rung groups are spaced uniformly about the first conductive ring, each of the plurality of rung groups comprises a plurality of conductive rungs extending between and connected to the first and second conductive rings, the plurality of conductive rungs of each of the plurality of rung groups are azimuthally separated from one another by a first azimuth angle, each of the plurality of rung groups is separated from a neighboring rung group by a spacing that forms a window, and each of the windows have a second azimuth angle that is greater than the first azimuth angle. In some embodiments, a first rung group of the plurality of rung groups comprises a first plurality of conductive rungs; and the first plurality of conductive rungs comprises a first conductive rung at an edge of a first window and a second conductive rung at an edge of a second window different than the first window. In some embodiments, the first plurality of conductive rungs comprises a third conductive rung disposed between the first conductive rung and the second conductive rung and disposed between the first window and the second window. In some embodiments, the first conductive rung is spaced from the third conductive rung by a distance; and the second conductive is spaced from the third conductive rung by the distance. In some embodiments, the first conductive rung is configured to carry a first current; the second conductive rung is configured to carry a second current; and the third conductive rung is configured to carry a third current that is less than or equal to the first current and less than or equal to the second current. In some embodiments, the first conductive rung comprises a first plurality of sub-rungs that extend between and are connected to the first and second conductive rings; the first plurality of sub-rungs are azimuthally separated from one another by a third azimuth angle that is less than the first azimuth angle; and the first plurality of sub-rungs are configured to collectively carry the first current. In some embodiments, the first plurality of sub-rungs comprises N individual sub-rungs; and each of the N individual sub-rungs is configured to carry about 1/N of the first current. In some embodiments, the second conductive rung comprises a second plurality of sub-rungs that extend between and are connected to the first and second conductive rings; the second plurality of sub-rungs are azimuthally separated from one another by the third azimuth angle; and the second plurality of sub-rungs are configured to collectively carry the second current. In some embodiments, each of the first plurality of sub-rungs comprises a first conductive portion and a second conductive portion that collectively extend between the first conductive ring and the second conductive ring; each of the first plurality of sub-rungs comprises a mode switching element; and each of the mode switching elements electrically couple together the first and second portions of a corresponding one of the first plurality of sub-rungs.

In some embodiments, the present disclosure provides a method for magnetic resonance imaging (MRI). The method comprises arranging a patient within a bore of an MRI scanner, wherein the MRI scanner comprises a birdcage coil that is disposed on a former that wraps around the bore. The birdcage coil comprises: a first conductive ring; a second conductive ring spaced from the first conductive ring by a first distance, wherein the first and second conductive rings are concentric about an axis that extends laterally through the bore; at least two rung groups that extend between the first and second conductive rings, wherein: each of the rung groups comprises at least two conductive rungs that extend in parallel between the first and second conductive rings, each of the at least two conductive rungs of each of the rung groups are azimuthally separated from one another by a first azimuth angle, each of the rungs groups are azimuthally separated from a neighboring rung group by an opening, and each of the openings have a second azimuth angle that is greater than the first azimuth angle. An electromagnetic beam is applied to the patient, wherein the electromagnetic beam passes through one or more of the openings as the electromagnetic beam travels toward the patient. A $B_1$ magnetic field is applied to a target area of the patient via the birdcage coil, wherein the $B_1$ magnetic field excites protons in a selected slice of the target area of the patient. MRI signals are received from the excited protons of the selected slice via a receive coil, and an MRI image of the selected slice is generated via the received MRI signals. In some embodiments, the method further comprises generating an image of the patient based on signals received in response to the electromagnetic beam. In some embodiments, each of the openings extends laterally between the first and second conductive rings by at least about 25 percent of the first distance; and the second azimuth angle is greater than or equal to 22.5 degrees. In some embodiments, the birdcage coil comprises a total number of rung groups that is equal to N; the birdcage coil comprises a total number of openings that is equal to M; and N is equal to M. In some embodiments, the former is a circular cylindrical-like former, an elliptical cylindrical-like former, a conical cylindrical-like former, a parabolic cylindrical-like former, a hyperbolic cylindrical-like former, or a flared cylindrical-like former.

In some embodiments, the present disclosure further provides a magnetic resonance imaging (MRI) radio frequency (RF) coil configured to operate in at least one of a transmit (Tx) mode or a receive (Rx) mode. The MRI RF coil comprises a birdcage coil comprising: a pair of conductive rings spaced apart from one another in a first direction, wherein the pair of conductive rings are concentric about an axis; a plurality of rung groups are connected to and extend between the pair of conductive rings, wherein: the plurality of rung groups are spaced uniformly about the pair of conductive rings, each of the plurality of rung groups comprises a plurality of conductive rungs that are connected in parallel between the pair of conductive rings, and each of the plurality of rung groups is azimuthally separated from a neighboring rung group by a spacing that defines a window. The MRI RF coil also comprises a RF shield surrounding the birdcage coil and the axis. In some embodiments, the RF shield comprises at least one conductive joint. In some embodiments, each of the conductive joints of the RF shield are disposed directly over one of the plurality of rung groups. In some embodiments, the RF shield is a low radiation attenuation metal mesh. In some embodiments, the low radiation attenuation metal mesh is an aluminum mesh, a stainless steel mesh, or a slotted perforated copper sheet. In some embodiments, the RF shield comprises a low radiation attenuation metal mesh material positioned disposed directly over the windows and a high radiation attenuation metal mesh material positioned directly over the plurality of rung groups.

The following includes definitions of selected terms employed herein. The definitions include various examples or forms of components that fall within the scope of a term and that may be used for implementation. The examples are not intended to be limiting. Both singular and plural forms of terms may be within the definitions.

The terminology used herein is for the purpose of describing particular embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used herein, specify the presence of stated features, integers, steps, operations, elements and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which embodiments belong. It will be further understood that terms (e.g., those defined in commonly used dictionaries) should be interpreted as having a meaning that is consistent with their meaning in the context of the relevant art and will not be interpreted in an idealized or overly formal sense unless expressly so defined herein.

In the above description, some components may be displayed in multiple figures carrying the same reference signs but may not be described multiple times in detail. A detailed description of a component may then apply to that component for all its occurrences.

The detailed descriptions presented herein may be presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, otherwise manipulated in a logic, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on refer to actions and processes of a computer system, logic, processor, or similar electronic device that manipulates and transforms data represented as physical and/or electronic quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

What is claimed is:

1. A magnetic resonance imaging (MRI) radio frequency (RF) coil configured to operate in at least one of a transmit (Tx) mode or a receive (Rx) mode, the MRI RF coil comprising:

a first conductive ring structure, wherein the first conductive ring structure extends laterally around an axis in a first closed loop path;

a second conductive ring structure spaced from the first conductive ring structure, wherein the second conductive ring structure extends laterally around the axis in a second closed loop path, and wherein the axis extends through a center point of the first conductive ring structure and a center point of the second conductive ring structure;

a plurality of rung groups extending between the first and second conductive ring structures, wherein:

the plurality of rung groups are spaced uniformly about the first conductive ring structure;

the plurality of rung groups respectively comprise pluralities of conductive rung structures;

the conductive rung structures of the pluralities of conductive rung structures extend between and are connected to the first and second conductive ring structures;

the MRI RF coil has a total number of conductive rung structures equal to a total number of conductive rung structures of the pluralities of conductive rung structures;

for each of the plurality of rung groups, their corresponding plurality of conductive rung structures are uniformly spaced by a first azimuth angle;

the plurality of rung groups are uniformly spaced by a plurality of windows;

each of the plurality of windows have a second azimuth angle that is greater than the first azimuth angle;

the conductive rung structures of the pluralities of conductive rung structures respectively extend circumferentially around the axis by a plurality of third azimuth angles;

a sum of the third azimuth angles of the plurality of third azimuth angles is equal to a first value;

a difference between the total number of conductive rung structures of the MRI RF coil minus a total number of rung groups of the plurality of rung groups is equal to a second value;
a product of the first azimuth angle multiplied by the second value is equal to a third value;
a product of the second azimuth angle multiplied by the total number of rung groups of the plurality of rung groups is equal to a fourth value; and
a sum of the first value, the third value, and the fourth value is equal to 360 degrees.

2. The MRI RF coil of claim 1, wherein:
a first rung group of the plurality of rung groups comprises a first plurality of conductive rung structures of the pluralities of conductive rung structures;
the first plurality of conductive rung structures comprises a first conductive rung structure at an edge of a first window of the plurality of windows and a second conductive rung structure at an edge of a second window of the plurality of windows; and
the second window is different than the first window.

3. The MRI RF coil of claim 2, wherein:
the first plurality of conductive rung structures comprises a third conductive rung structure disposed between the first conductive rung structure and the second conductive rung structure and disposed between the first window and the second window.

4. The MRI RF coil of claim 3, wherein:
the first conductive rung structure is configured to carry a first current;
the second conductive rung structure is configured to carry a second current; and
the third conductive rung structure is configured to carry a third current that is less than or equal to the first current and less than or equal to the second current.

5. The MRI RF coil of claim 4, wherein:
the first conductive rung structure comprises a first plurality of sub-rung structures that extend between and are connected to the first and second conductive ring structures; and
the first plurality of sub-rung structures are uniformly spaced by a fourth azimuth angle that is less than the first azimuth angle;
the first plurality of sub-rung structures are configured to collectively carry the first current;
the first plurality of sub-rung structures comprises N individual sub-rung structures;
N minus 1 is equal to a fifth value;
the N individual sub-rung structures extend circumferentially around the axis by a plurality of fifth azimuth angles;
a sum of the fifth azimuth angles of the plurality of fifth azimuth angles is equal to a sixth value;
a product of the fourth azimuth angle multiplied by the fifth value is equal to a seventh value; and
a sum of the first value, the third value, the fourth value, the sixth value, and the seventh value is equal to 360 degrees.

6. The MRI RF coil of claim 5, wherein:
each of the N individual sub-rung structures is configured to carry about 1/N of the first current.

7. The MRI RF coil of claim 5, wherein:
each of the first plurality of sub-rung structures comprises a first conductive portion and a second conductive portion that collectively extend between the first conductive ring structure and the second conductive ring structure;
each of the first plurality of sub-rung structures comprises a mode switching element; and
each of the mode switching elements electrically couple together the first and second conductive portions of a corresponding one of the first plurality of sub-rung structures.

8. The MRI RF coil of claim 5, wherein:
the N individual sub-rung structures have first widths;
the third conductive rung structure has a second width; and
the second with is greater than each of the first widths.

9. The MRI RF coil of claim 1, wherein each of the plurality of rung groups comprises a same amount of the conductive rung structures.

10. The MRI RF coil of claim 1, wherein:
the plurality of windows has a total number of windows; and
the total number of windows is equal to an even number.

11. The MRI RF coil of claim 1, wherein:
a RF shield surrounds the MRI RF coil and the axis, wherein the RF shield comprises:
a low radiation attenuation material positioned directly over the plurality of windows; and
a high radiation attenuation material positioned directly over the plurality of rung groups, wherein the high radiation attenuation material has a higher radiation attenuation relative to the low radiation attenuation material.

12. A method for magnetic resonance imaging (MRI) comprising:
providing an MRI scanner, wherein the MRI scanner comprises a birdcage coil that is disposed on a former that wraps around a bore of the MRI scanner, and wherein the birdcage coil comprises:
a first conductive ring structure;
a second conductive ring structure spaced from the first conductive ring structure by a first distance, wherein the first and second conductive ring structures are concentric about an axis that extends laterally through the bore;
at least two rung groups that extend between the first and second conductive ring structures, wherein:
each of the at least two rung groups comprises at least two conductive rung structures that extend in parallel between the first and second conductive ring structures;
for each of the at least two rung groups, the at least two conductive rung structures are uniformly spaced by a first azimuth angle;
the at least two rung groups are uniformly spaced by a plurality of openings;
a total number of openings of the plurality of openings is equal to a total number of rung groups of the at least two rung groups; and
each of the openings of the plurality of openings have a second azimuth angle that is greater than the first azimuth angle;
arranging a patient within the bore of the MRI scanner;
applying an electromagnetic beam to the patient that passes through one or more of the openings as the electromagnetic beam travels toward the patient;
applying a $B_1$ magnetic field to a target area of the patient via said birdcage coil, wherein the $B_1$ magnetic field excites protons in a selected slice of the target area of the patient;
receive MRI signals from the excited protons of the selected slice via a receive coil; and
generate an MRI image of the selected slice via the received MRI signals.

13. The method of claim 12, further comprising:
generating an image of the patient based on signals received in response to the electromagnetic beam.

14. The method of claim 13, wherein:
the electromagnetic beam is applied to the patient via an electromagnetic beam generator;
the signals received in response to the electromagnetic beam are received by an electromagnetic beam detector;
the electromagnetic beam generator is positioned directly over a first opening of the plurality of openings;
the electromagnetic beam detector is positioned directly over a second opening of the plurality of openings; and
the electromagnetic beam generator and the electromagnetic beam detector are azimuthally separated by 180 degrees.

15. The method of claim 12, wherein:
each of the openings of the plurality of openings extends laterally between the first and second conductive ring structures by at least about 25 percent of the first distance; and
the second azimuth angle is greater than or equal to 22.5 degrees.

16. The method of claim 12, wherein the MRI scanner further comprises:
a radio frequency (RF) shield surrounding the birdcage coil and the axis, wherein the RF shield comprises:
a low radiation attenuation material positioned directly over the plurality of openings; and
a high radiation attenuation material positioned directly over the at least two rung groups, wherein the high radiation attenuation material has a higher radiation attenuation relative to the low radiation attenuation material.

17. A magnetic resonance imaging (MRI) radio frequency (RF) coil configured to operate in at least one of a transmit (Tx) mode or a receive (Rx) mode, the MRI RF coil comprising:
a birdcage coil comprising:
a pair of conductive rings spaced apart from one another in a first direction, wherein the pair of conductive rings are concentric about an axis;
a plurality of rung groups connected to and extending between the pair of conductive rings, wherein:
the plurality of rung groups are spaced uniformly about the pair of conductive rings;
each of the plurality of rung groups comprises a plurality of conductive rungs that are connected in parallel between the pair of conductive rings; and
each of the plurality of rung groups is azimuthally separated from a neighboring rung group by a spacing that defines a window; and
a RF shield surrounding the birdcage coil and the axis, wherein the RF shield comprises:
a low radiation attenuation material positioned directly over the windows; and
a high radiation attenuation material positioned directly over the plurality of rung groups, wherein the high radiation attenuation material has a higher radiation attenuation relative to the low radiation attenuation material.

18. The MRI RF coil of claim 17, wherein the RF shield comprises at least one conductive joint.

19. The MRI RF coil of claim 18, wherein each of the at least one conductive joint of the RF shield is disposed directly over one of the plurality of rung groups.

20. The MRI RF coil of claim 17, wherein the low radiation attenuation material is an aluminum mesh, a stainless steel mesh, or a slotted perforated copper sheet.

* * * * *